(12) United States Patent
Vivek et al.

(10) Patent No.: US 11,866,694 B2
(45) Date of Patent: Jan. 9, 2024

(54) METHOD AND SYSTEM FOR DISSOCIATING BIOLOGICAL TISSUE INTO SINGLE CELLS USING ULTRASONIC ENERGY

(71) Applicant: Microsonic Systems Inc., San Jose, CA (US)

(72) Inventors: Vibhu Vivek, Santa Clara, CA (US); Poonam Sansanwal, San Ramon, CA (US)

(73) Assignee: Microsonic Systems Inc., San Jose, CA (US)

( * ) Notice: Subject to any disclaimer, the term of this patent is extended or adjusted under 35 U.S.C. 154(b) by 429 days.

(21) Appl. No.: 17/061,337

(22) Filed: Oct. 1, 2020

(65) Prior Publication Data
US 2021/0102187 A1 Apr. 8, 2021

Related U.S. Application Data

(60) Provisional application No. 62/909,484, filed on Oct. 2, 2019.

(51) Int. Cl.
| | |
|---|---|
| *C12N 13/00* | (2006.01) |
| *C12M 3/08* | (2006.01) |
| *C12M 1/00* | (2006.01) |

(52) U.S. Cl.
CPC ............... *C12N 13/00* (2013.01); *C12M 3/08* (2013.01); *C12M 41/14* (2013.01)

(58) Field of Classification Search
None
See application file for complete search history.

(56) References Cited

U.S. PATENT DOCUMENTS

| | | | |
|---|---|---|---|
| 5,879,939 A * | 3/1999 | Gray | A61K 35/39 435/378 |
| 6,682,214 B1 | 1/2004 | Vivek | |
| 8,319,398 B2 | 11/2012 | Vivek | |
| 2004/0173024 A1 | 9/2004 | Mckeon | |
| 2021/0102875 A1 | 4/2021 | Levers et al. | |

FOREIGN PATENT DOCUMENTS

| | | | |
|---|---|---|---|
| CN | 102917756 A | 2/2013 | |
| WO | WO-0121291 A2 * | 3/2001 | .......... B01F 13/0001 |
| WO | 2009124290 A1 | 10/2009 | |
| WO | 2011148314 A1 | 12/2011 | |
| WO | 2013056062 A1 | 4/2013 | |

OTHER PUBLICATIONS

International Search Report and Written Opinion of the International Searching Authority dated Feb. 12, 2021, for International Patent Application No. PCT/US20/53798, filed on Oct. 1, 2020, 16 pages.

Invitation to Pay Additional Fees dated Dec. 11, 2020, for International Patent Application No. PCT/US20/53798, filed Oct. 1, 2020, 2 pages.

Vivek, V. et al. (2000). "Novel Acoustic-Wave Micromixer," Proceedings IEEE Thirteenth Annual International Conference on Micro Electro Mechanical Systems (Cat. No.00CH36308), Miyazaki, Japan, 2000, pp. 668-673, PDF located at http://mems.usc.edu/Micromixer_MEMS2000.pdf, last visited on Feb. 18, 2021, 6 pages.

\* cited by examiner

*Primary Examiner* — David W Berke-Schlessel
(74) *Attorney, Agent, or Firm* — Morrison & Foerster LLP

(57) ABSTRACT

A method of dissociating single cells from a biological tissue sample is described herein, along with systems for performing such methods. The method includes generating one or more ultrasonic wave pulses using a transducer comprising one or more Fresnel Annular Sector Actuator (FASA) elements; and applying energy from the generated one or more ultrasonic wave pulses to a sample container holding the biological tissue sample through a coupling medium that couples the one or more FASA elements to the sample container to dissociate single cells from the biological tissue is described herein.

29 Claims, 12 Drawing Sheets

METHOD AND SYSTEM FOR DISSOCIATING BIOLOGICAL TISSUE INTO SINGLE CELLS USING ULTRASONIC ENERGY

CROSS-REFERENCE TO RELATED APPLICATION

This application claims the priority benefit of U.S. Provisional Application No. 62/909,484, filed on Oct. 2, 2019; the contents of which are incorporated herein by reference for all purposes.

FIELD OF THE INVENTION

Described herein are methods and systems for dissociating single cells from a biological tissue sample using ultrasonic energy.

BACKGROUND OF THE INVENTION

In the fields of medicine and biological research, many current analyses are carried out by techniques that treat each tumor sample as a homogeneous mass, despite the knowledge that tumor tissue is a heterogeneous mass of cancer cells, e.g. infiltrating immune cells and tumor stroma. The mass approach provides large amounts of molecular information but retain no context with respect to the cellular components in the original sample. These results are an average of the entire tumor tissue, which precludes identification of rare subpopulations of important cells. It has been suggested that information lost by this practice may conceal crucial insights into tumor progression, metastasis, and drug resistance. Plus, a tumor's microenvironment includes of a diverse array of cell types that maintain homeostasis and drive further development. This intra-tumor cellular heterogeneity has been identified as a key factor underlying progression, metastasis, and the development of drug resistance.

Flow sorting methods have been developed because they offer high-throughput and multiplexed information about each cell within the sample. Cell sorting can also be used to isolate rare cell types such as cancer stem cells, metastatic precursors, and drug resistance clones for additional study. However, for single cell analysis, tissue must first be broken down into viable single cells, without affecting the phenotype and genotype information which requires considerable time and effort.

Previously, tumor tissue has been dissociated into single cells using proteolytic enzymes in combination with some form of physical force to digest cellular adhesion molecules and/or the underlying extracellular matrix. However, not all cell types can be easily dissociated using enzymes. For those cell types that are susceptible to enzymatic dissociation, it has been shown that enzymes can be detrimental to the cells and negatively impact the ability of the generated single cells to subsequently survive and or divide. For example, enzymatic dissociation generally includes incubating the tissue at an elevated temperature (e.g., 37° C.), which can result in the undesirable expression of pro-inflammatory and/or stressed induced genes. The expression of these genes can significantly alter the state of the cells from its native state.

SUMMARY OF THE INVENTION

Described herein is a method of dissociating single cells from a biological tissue sample, and a system for dissociating sing cells from a biological tissue sample, using a transducer with one or more Fresnel Annular Sector Actuator (FASA) elements that generate bulk lateral ultrasonic energy.

In some embodiments, a method of dissociating single cells from a biological tissue sample comprises generating one or more ultrasonic wave pulses using a transducer comprising one or more Fresnel Annular Sector Actuator (FASA) elements; and applying energy from the one or more generated ultrasonic wave pulses to a biological tissue sample contained by a sample container through a coupling medium that couples the one or more FASA elements to the sample container to dissociate single cells from the biological tissue.

In some embodiments, a method of dissociating single cells from a biological tissue sample comprises generating one or more ultrasonic wave pulses using a transducer comprising one or more Fresnel Annular Sector Actuator (FASA) elements; applying energy from the one or more generated ultrasonic wave pulses to a biological tissue sample contained by a sample container through a coupling medium that couples the one or more FASA elements to the sample container to dissociate single cells from the biological tissue; and controlling the temperature of the biological tissue sample while the energy from the one or more generated ultrasonic wave pulses is applied to the biological tissue sample.

In some embodiments, the temperature of the biological tissue sample is controlled to between about 2° C. and about 70° C. In some embodiments, controlling the temperature of the biological tissue sample reduces the expression of one or more pro-inflammatory or stressed-induced genes compared to not controlling the temperature of the biological tissue sample. In some embodiments, the one or more pro-inflammatory or stressed-induced genes is selected from the group consisting of CD69, LRRK2, TNF, FOS, PDE4B, NR4A3, S100A9, S100A8, THBD, IL-1β, IL-1α, HK2, CXCL8, CXCL1, AREG, ERG2, TIMP1, and CXCR4.

In some embodiments of the above methods, controlling the temperature of the biological tissue sample comprises controlling the temperature of the coupling medium. In some embodiments, the temperature of the coupling medium is controlled to cool the biological tissue sample or limit a temperature increase of the biological tissue sample. In some embodiments, the coupling medium is controlled to a temperature between about 2° C. and about 70° C. In some embodiments, the coupling medium is controlled to a temperature between about 2° C. and about 25° C.

In some embodiments of the above methods, controlling the temperature of the biological tissue sample comprises heating the biological tissue sample using the energy from the one or more generated ultrasonic wave pulses. In some embodiments, a first portion of the one or more ultrasonic wave pulses generated by the transducer are configured to heat the biological tissue sample and a second portion of the one or more ultrasonic wave pulses generated by the transducer are configured to not heat the biological tissue sample. In some embodiments, the biological tissue sample is heated to a peak temperature between about 20° C. and about 70° C.

In some embodiments of the above methods, the biological tissue sample is heated by less than 15° C. or is not heated during the application of energy from the one or more generated ultrasonic wave pulses to the sample container.

In some embodiments of the above methods, the coupling medium is a liquid, a solid, or a gel. In some embodiments, the coupling medium is a liquid, and the method further comprises cycling the coupling fluid through a temperature controller.

In some embodiments of the above methods, about 20% or more of the dissociated single cells are viable. In some embodiments, about 20% to about 95% of the dissociated single cells are viable. In some embodiments, two or more different types of viable cells are dissociated from the biological tissue sample.

In some embodiments of the above methods, the biological tissue sample comprises a cancer tissue.

In some embodiments of the above methods, the method comprises selecting one or more of a repetition rate, a pulse duration, a duty cycle, a peak power, or a total duration for the one or more generated ultrasonic wave pulses. In some embodiments, the energy applied to the sample does not result in a shear force applied to the sample. In some embodiments, the energy applied to the sample results in a mixing force or a suspending force applied to the sample.

In some embodiments, a plurality of ultrasonic wave pulses are generated at a repetition rate of about 1 Hz to about 100,000 Hz.

In some embodiments, the one or more ultrasonic wave pulses are generated at a duty cycle of about 0.1% to about 95%.

In some embodiments, energy from the one or more ultrasonic wave pulses is applied to the coupling medium for about 2 seconds to about 90 minutes.

In some embodiments of the above methods, the biological tissue is suspended in a liquid within the sample container.

In some embodiments of the above methods, the biological tissue is minced.

In some embodiments of the above methods, the biological tissue sample is substantially free of non-endogenous proteases.

In some embodiments of the above methods, the transducer comprises four or more FASA elements.

In some embodiments of the above methods, the biological tissue sample is an unpreserved sample.

Also described herein is a system for dissociating single cells from a biological tissue sample, comprising a transducer comprising one or more Fresnel Annular Sector Actuator (FASA) elements configured to generate one or more ultrasonic wave pulses; a sample container configured to hold the biological tissue sample; and a coupling medium configured to couple the one or more FASA elements to the sample container and transmit energy from the plurality of ultrasonic wave pulses generated by the transducer to the sample container to dissociate single cells from the biological tissue sample.

Further described is a system for dissociating single cells from a biological tissue sample, comprising a transducer comprising one or more Fresnel Annular Sector Actuator (FASA) elements configured to generate one or more ultrasonic wave pulses; a sample container configured to hold the biological tissue sample, wherein the system is configured to control the temperature of the biological tissue sample; and a coupling medium configured to couple the one or more FASA elements to the sample container and transmit energy from the plurality of ultrasonic wave pulses generated by the transducer to the sample container to dissociate single cells from the biological tissue sample. In some embodiments, the system is configured to control the temperature of the biological sample to a temperature between about 2° C. and about 70° C.

In some embodiments of the systems described above, the system further includes a temperature controller configured to control the temperature of the coupling medium. In some embodiments, the temperature controller is configured to control the coupling medium to a temperature between about 2° C. and about 70° C. In some embodiments the temperature control is configured to cool the coupling medium to a temperature between about 2° C. and about 25° C.

In some embodiments of the systems described above, the coupling medium is a liquid, and the system further comprises a pump configured to circulate the coupling medium between a position between the transducer and the sample container, and the temperature controller.

In some embodiments of the systems described above, the system is configured to control the temperature of the biological tissue sample by heating the biological tissue sample using energy from the one or more generated ultrasonic wave pulses.

In some embodiments of the systems described above, the transducer is configured selectively generate (1) one or more ultrasonic wave pulses that heat the biological tissue sample and (2) one or more ultrasonic wave pulses that do not heat the sample.

In some embodiments of the systems described above, the system further comprises a control module configured to operate the transducer to generate the one or more ultrasonic wave pulses. In some embodiments, the control module is configured to operate the transducer to generate the plurality of ultrasonic wave pulses at one or more of a selected repetition rate, a selected pulse duration, a selected duty cycle, a selected peak power, a selected average pulse power, or a selected total duration. In some embodiments, the control module is configured to operate the transducer to generate a plurality of ultrasonic wave pulses at a repetition rate of about 1 Hz to about 100,000 Hz. In some embodiments, the control module is configured to operate the transducer to generate the one or more ultrasonic wave pulses at a duty cycle of about 0.1% to about 95%. In some embodiments, the control module is configured to operate the transducer to generate the one or more ultrasonic wave pulses for a total duration of about 2 seconds to about 90 minutes. In some embodiments, the control module comprises a radio-frequency (RF) generator configured to operate the transducer to generate the ultrasonic wave pulses. In some embodiments, the control module is configured to operate the transducer to generate the one or more ultrasonic wave pulses so that a shear force is not applied to the sample. In some embodiments, the control module is configured to operate the transducer to generate the one or more ultrasonic wave pulses so that a mixing force or a suspending force is applied to the sample.

In some embodiments of the systems described above, the transducer comprises four or more FASA elements.

In some embodiments of the systems described above, the system is disposed in an array comprising a plurality of systems.

BRIEF DESCRIPTION OF THE DRAWINGS

The foregoing summary, as well as the following detailed description of embodiments, is better understood when read in conjunction with the appended drawings. For the purpose of illustrating the present disclosure, the drawings show example embodiments of the disclosure; the disclosure, however, is not limited to the specific methods and instrumentalities disclosed. In the drawings.

DETAILED DESCRIPTION OF THE INVENTION

Figure 1:
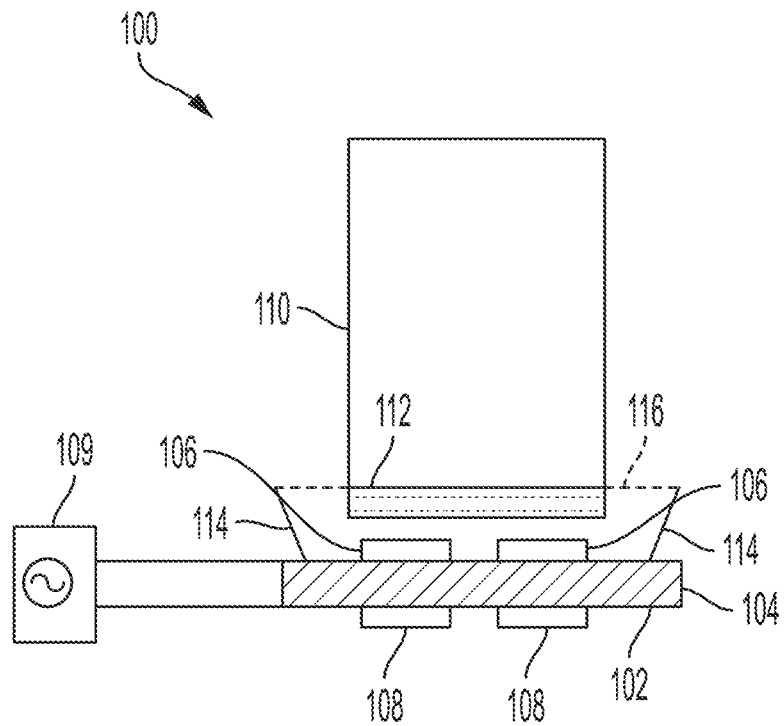
FIG. 1 shows an exemplary system for dissociating cells from a biological tissue sample.

Described herein is a method of dissociating single cells from a biological tissue sample using ultrasonic energy emitted from an ultrasonic transducer, and systems for performing such methods. The ultrasonic transducer includes one or more Fresnel Annular Sector Actuator (FASA) elements, which allow for bulk lateral ultrasonic energy to be applied to the biological tissue sample held in a sample container.

A FASA transducer can be used to apply energy to the biological sample provides a thorough but gentle application of energy that separates individual cells while minimizing cell lysis, a common issue when applying traditional ultrasonic energy to tissue. Accordingly, an increased proportion of single cells separated from the tissue is viable and/or can express proteins compared to traditional ultrasonic energy applications. Additionally, the methods described herein allow for more faster and more thorough cell dissociation than methods that include the use of enzymes (such as proteases) to separate cells from a biological tissue sample, while also avoiding enzyme-induced alterations of the in vivo state of the cells.

The bulk lateral ultrasonic waves generated by the FASA elements can be configured to apply one or more of (or configured to not apply one or more of) a mixing force, a suspension force, a shearing force, or a heating energy. The energy from the emitted ultrasonic waves used to dissociate single cells from the biological tissue, for example, can apply mixing and/or suspension forces to the biological tissue sample, thereby dissociating single cells from the biological tissue sample. At the same time the ultrasonic energy applied to the sample may be applied to avoid the application of shear forces, which can result in cell lysis.

The temperature of the sample can be controlled during single cell dissociation, which can limit expression of pro-inflammatory and/or stress-induced genes. Heating of the sample for extended periods of time can result in the expression of pro-inflammatory and/or stress induced genes, which can alter the biological state of the cells. For example, heating the tissue to 37° C. during enzymatic cell dissociation induces the pro-inflammatory and stressed induced gene expression. Short bursts of heat applied to the sample, however, may aid tissue dissociation while limiting the expression of pro-inflammatory or stress-induced genes. Thus, in some embodiments, the ultrasonic energy applied to the sample is configured to apply a heating energy to the sample. The heating energy can controllably warm the sample for a desired duration, which may be less than the total duration of ultrasonic energy applied to the cells.

In some embodiments, a coupling medium is used to control the temperature of the sample, for example to decrease the temperature of the sample heated by the applied ultrasonic energy (or to counter an increase in temperature resulting from heating by the applied ultrasonic energy so that it does not increase as much as it would without controlling the temperate using the coupling medium). The coupling medium can absorb heat from the sample, for example, and a temperature controller can be used to control the temperature of the coupling medium. In some embodiments, the sample is warmed through the coupling medium, which can be heated by the temperature controller.

Biological tissue samples frequently have a heterogeneous cell population, including two or more different cell types. Using the methods described herein single, viable cells can be dissociated from the biological tissue sample, wherein the single cells are within a heterogeneous viable cell population. Previously known methods of dissociating cells often results in preferential cell lysis, which can destroy certain cell types from the heterogeneous biological tissue sample. In some embodiments, the method results in two or more different types of viable cells dissociated from the sample (such as a cancer sample).

In an exemplary method, dissociating single cells from a biological tissue sample can include generating a generating a plurality of ultrasonic wave pulses using a transducer comprising one or more Fresnel Annular Sector Actuator (FASA) elements; and applying energy from the generated plurality of ultrasonic wave pulses to a sample container holding the biological tissue sample through a coupling medium that couples the one or more FASA elements to the container, thereby dissociating single cells from the biological tissue.

In another exemplary method of dissociating single cells from a biological tissue sample, the method comprises generating one or more ultrasonic wave pulses using a transducer comprising one or more Fresnel Annular Sector Actuator (FASA) elements; applying energy from the one or more generated ultrasonic wave pulses to a sample container holding the biological tissue sample through a coupling medium that couples the one or more FASA elements to the sample container to dissociate single cells from the biological tissue; and controlling the temperature of the biological tissue sample while the energy from the one or more generated ultrasonic wave pulses is applied to the sample container. Controlling the temperature of the biological tissue sample may reduce the expression of one or more pro-inflammatory or stressed-induced genes compared to not controlling the temperature of the biological tissue sample.

In an exemplary system for dissociating single cells from a biological sample, the system can include a transducer comprising one or more Fresnel Annular Sector Actuator (FASA) elements configured to generate a plurality of ultrasonic wave pulses; a sample container configured to hold the biological tissue sample; and a coupling medium configured to couple the one or more FASA elements to the container and transmit energy from the plurality of ultrasonic wave pulses generated by the transducer to the container, which thereby dissociate single cells from the biological tissue sample.

In another exemplary system for dissociating single cells from a biological tissue sample, the system comprises a transducer comprising one or more Fresnel Annular Sector Actuator (FASA) elements configured to generate one or more ultrasonic wave pulses; a sample container configured to hold the biological tissue sample, wherein the system is configured to control the temperature of the biological tissue sample; and a coupling medium configured to couple the one or more FASA elements to the sample container and transmit energy from the plurality of ultrasonic wave pulses generated by the transducer to the sample container to dissociate single cells from the biological tissue sample.

Definitions

As used herein, the singular forms "a," "an," and "the" include the plural references unless the context clearly dictates otherwise.

Reference to "about" a value or parameter herein includes (and describes) variations that are directed to that value or parameter per se. For example, description referring to "about X" includes description of "X".

A "viable" cell refers to a cell that is alive and capable of cellular growth or expansion in a culture medium.

It is understood that aspects and variations of the invention described herein include "consisting" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

The section headings used herein are for organization purposes only and are not to be construed as limiting the subject matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The disclosures of all publications, patents, and patent applications referred to herein are each hereby incorporated by reference in their entireties. To the extent that any reference incorporated by reference conflicts with the instant disclosure, the instant disclosure shall control.

System for Dissociating Cells from Biological Tissue

The system for dissociating cells form a biological tissue sample includes a transducer, a sample container, and a coupling medium. The transducer includes one or more Fresnel Annular Sector Actuator (FASA) elements, which are configured to generate ultrasonic wave pulses. The sample container can hold the biological tissue sample, and the coupling medium is positioned to couple the one or more FASA elements to the container at a defined distance. When the transducer emits the ultrasonic wave pulses, the coupling medium transmits energy from the ultrasonic waves to the container, which allows for the dissociation of single cells from the biological tissue sample.

In some embodiments of the system for dissociating single cells from a biological tissue sample, the system is configured to control the temperature of the biological tissue sample. For example, the system may be configured to control the temperature of the biological tissue sample to between about 2° C. to about 70° C. (such as between about 2° C. and about 5° C., between about 5° C. and about 10° C., between about 10° C. and about 15° C., between about 15° C. and about 25° C., between about 25° C. and about 35° C., between about 35° C. and about 45° C., between about 45° C. and about 55° C., or between about 55° C. and about 70° C.).

FIG. 1 shows a side view of an exemplary system 100 that includes a transducer 102 and a sample container 110 for an example embodiment. The transducer 102 includes a piezoelectric material 104 sandwiched between a top electrode 106 and a bottom electrode 108. As discussed below, the electrodes 106 and 108 are configured as a Fresnel Annular Sector Actuator (FASA) that directs ultrasonic waves in a target direction (e.g., upwards in FIG. 1) when in operation. A control module 109 is configured to operate the transducer to produce the ultrasonic waves. The sample container 110 contains a biological tissue sample 112, which may be suspended in a liquid (e.g., water or a buffer). The system 100 further includes a coupling medium 114 configured to couple the transducer 104 to enclose to the sample container 110. The coupling medium may be held within sidewalls of the system. The biological tissue sample 112 within the sample container 110 is optionally below the surface 116 of the coupling medium 114. The coupling medium 114 provides acoustic coupling between the transducer 104 and the sample container 110 such that it transmits energy from the ultrasonic waves emitted by the transducer 102 to the sample container, which dissociates single cells from the biological tissue sample 112 within the sample container 110.

The Fresnel Annular Sector Actuator (FASA) element(s) of the transducer allow the transducer to emit ultrasonic waves that have a high lateral acoustic potential profile directed in a target direction, which allows for mixing of fluids (e.g., a liquid holding the biological tissue sample) within the target direction. Exemplary FASA elements are described in U.S. Pat. No. 6,682,214 or Vivek et al., *Novel Acoustic-Wave Micromixer*, Proceedings MEMS 2000, pp. 668-673 (2000). The FASA is based on a self-focusing acoustic wave transducer which focuses acoustic waves through constructive wave interference. Strong ultrasonic waves are generated over an electrode area, and the ultrasonic waves interfere with each other as they propagate. This causes mixing of fluid present in the target direction. The mixing can be enhanced by providing selective activation of the different FASA elements. That is, one or more of the FASA elements can be independently operated.

Electrodes of the FASA elements can sandwich a piezoelectric material, such as lead zirconate titanate (PZT), $BaTiO_3$, $KNbO_3$ and the like. Electrical current passing through the electrodes activates the piezoelectric material, thereby causing the transducer to generate the ultrasonic waves. The electrodes of the FASA element are configured in one or more annular ring segments. When an annular ring is broken into angled segments, there are proportionate changes in the vertical and lateral acoustic potential profile. More specifically, as the angle of the sector profile gets smaller, the gradient of the lateral acoustic potential becomes greater and the vertical potential profile becomes more distributed. The angle of the FASA element may be between more than 0° and less than 360°, for example up to about 10°, about 10° to about 20°, about 20° to about 45°, about 45° to about 60°, about 60° to about 75°, about 75° to about 90°, about 90° to about 105°, about 105° to about 120°, about 120° to about 135°, about 135° to about 150°, about 150° to about 165°, about 165° to about 180°, about 180° to about 210°, about 210° to about 240°, about 240° to about 270°, about 270° to about 300°, about 300° to about 330°, or about 330° to less than 360°. In some embodiments, the angle of the FASA element is about 75° to about 105°. In some embodiments, the angle of the FASA element is about 90°.

Figure 2:
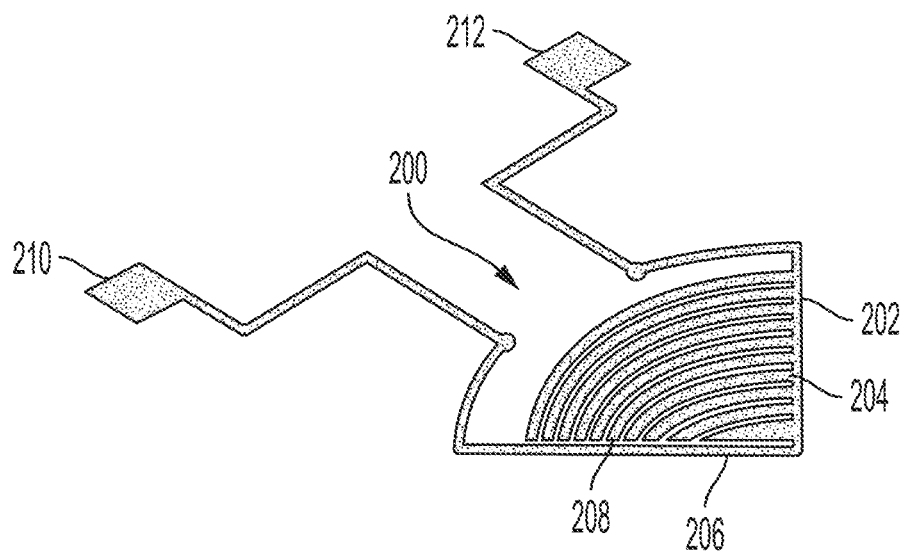
FIG. 2 shows an electrode pattern of a FASA element that may be used with the transducer of the system described herein.

The electrodes of the FASA element is patterned by one annular segment, or by a plurality of concentric annular segment arranged in a Fresnel lens pattern. For example, the electrode of the FASA element may include 2, 3, 4, 5, 6, 7, 8, 9, 10, or more concentric annular segments. The FASA element is operated by driving a current through the electrode via the electrode terminals, for example by operating a control module to pass the current. FIG. 2 illustrates an electrode pattern of a FASA element that may be used with the transducer of the system described herein. The angle of the FASA element 200 in this exemplary embodiment is 90° as defined by the edges of the FASA element 202 and 206. The FASA element includes an electrode configured with a plurality of concentric annular segments (e.g., 204 and 208). The electrode includes terminals 210 and 212 through which the control module can drive a current. The electrode sandwiches a piezoelectric material (see FIG. 1), which generates the electric waves when the current passes through the electrode.

The transducer of the system may have one or a plurality of FASA elements directing ultrasonic waves in the direction of the sample container. For example, the transducer may include 1, 2, 3, 4, 5, 6, 7, 8, 9, 10 or more FASA elements configured to emit ultrasonic waves in the direction of the sample container. The FASA elements may be arranged in a circular pattern, with the apex of FASA elements positioned proximal to the center of the circle. In some embodiments, the diameter of the circular pattern is about 5 mm to about 20 mm in diameter (for example, about 5 mm to about 7 mm in diameter to about 9 mm in diameter, about 9 mm in diameter to about 11 mm in diameter, about 11 mm in diameter to about 13 mm in diameter, about 13 mm in diameter to about 15 mm in diameter, about 15 mm in diameter to about 17 mm in diameter, or about 17 mm in diameter to about 20 mm in diameter), The FASA elements of the transducer may be separated by a gap, which may be consistent along the radius of the FASA or may vary depending on the configuration of the FASA elements on the transducer. In some embodiments, two or more of the FASA elements are overlapping.

A plurality of FASA elements on the same transducer (or a portion of the FASA elements) may be activated to generate ultrasonic simultaneously or non-simultaneously (for example, sequentially or alternating activation of two or more FASA elements). By proper control of the FASA element activation, a random or controlled mixing is achieved. In some embodiments, 50%, or more than 50% of the FASA element of the same transducer are activated simultaneously. In some embodiments, 75% or more than 75% of the FASA element of the same transducer are activated simultaneously (e.g., 3 of 4 FASA elements). In some embodiments, all of the FASA elements of the same transducer are activated simultaneously. When less than all FASA elements are simultaneously activated, the one or more non-active FASA elements may alternate among all FASA elements of the transducer during operation.

Figure 3:
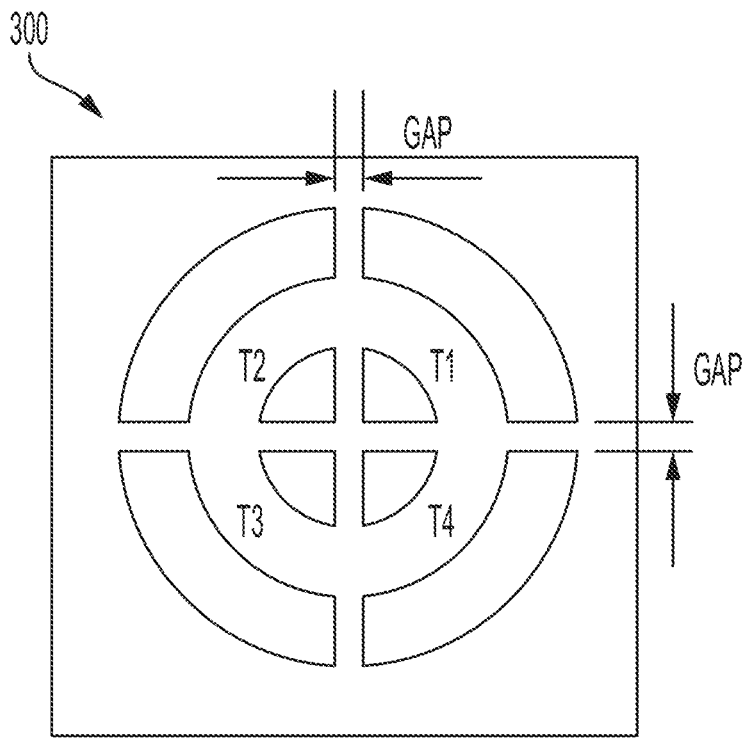
FIG. 3 shows a top view of an exemplary ultrasonic transducer with four 90-degree FASA elements, which may be used with the system for dissociating single cells from a biological tissue sample as described herein.

FIG. 3 shows a top view of an ultrasonic transducer 300 with four 90-degree FASA elements labeled as T1, T2, T3, and T4. The small gap between the FASA elements allows the FASA elements to effectively combine the mechanical effects to generate lateral mixing forces. The individual FASA elements may be independently operated.

Figure 4:
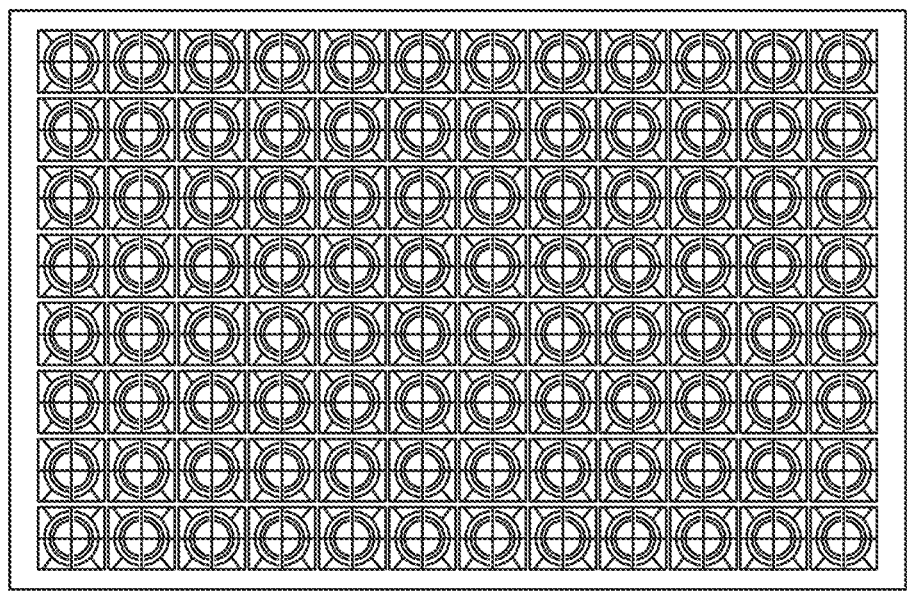
FIG. 4 shows an exemplary 8×12 transducer array with 96 transducer units disposed therein, each unit having four FASA elements.

The transducer may be an isolated transducer or may be disposed in a transducer array. The transducer array may include a plurality of separated piezoelectric elements or may have a common (i.e., shared) piezoelectric elements that are configured with one or more FASA elements to form separate transducer units. An exemplary transducer array is described in U.S. Pat. No. 8,319,398. FIG. 4 illustrates an exemplary 8×12 transducer array with 96 transducer units disposed therein, each unit having four FASA elements. Arrays with any number of transducers may be used, for example, between 1 and 1000 transducers within the array. The number of transducers within the array may match, for example, a number of wells in a multi-well plate used for the sample container (e.g., 96-transducer array can be used with a 96-well plate, or a 384-transducer array can be used with a 384-well plate).

A control module can be used to operate the FASA elements of the transducers using one or more selected parameters to generate ultrasonic waves. The control module can include, for example, a radiofrequency (RF) generator, which can induce a current through the FASA element electrodes. In some embodiments, the control module includes an amplifier, which can amplify the RF signal generated by the RF generator to operate the transducer. The control module may also include one or more additional electronic circuits configured to adjust one or more parameters of ultrasonic waves emitted by the transducer, for example by controlling the RF signal. The control module may control, for example, the peak power, pulse repletion rate, RF frequency, duty cycle, pulse duration, total duration, etc. of the RF energy applied to the ultrasonic transducer, which controls the ultrasonic waves emitted from the transducer. The control module can include a user interface (which may include, for example, one or more buttons, switches, or digital interfaces), which may be used to select the one or more control module parameters. The parameters of the electrical signal flowing through the FASA element electrode controls the resulting ultrasonic waves generated by the transducer. The frequency of the drive current flowing through the electrodes of the FASA element can based on the resonant frequency of the piezoelectric material to enhance the generation of ultrasonic waves (e.g., within 10%, within 20%, or within 30% of a resonant frequency or higher). The shape of the drive current may be sinusoidal, square, or any other suitable shape.

The selected parameters for controlling the RF energy applied to the ultrasonic transducer can affect the type of ultrasonic waves generated by the ultrasonic transducer. The FASA element generates bulk lateral ultrasonic waves, which can be configured to generate one or more of a mixing force, a suspending force, a shearing force, and a heating energy. The mixing and suspending forces are generally beneficial for dissociating single cells from the tissue sample, whereas shearing force can result in cell lysis and is preferably avoided. Optionally the bulk lateral ultrasonic waves generated by the transducer can be configured to apply a heating energy to the biological tissue sample, which can be applied to control the temperature of the biological tissue sample. In some embodiments, the energy from the ultrasonic waves does not apply a heating energy to the biological tissue sample. The energy from the ultrasonic waves applied to the biological tissue sample may be heterogeneous during the cell dissociation process. For example, a first portion of the ultrasonic waves may apply a heating energy to the biological tissue sample, and a second portion of the ultrasonic waves does not apply a heating energy to the biological tissue sample.

The control module may be configured to operate the transducer to generate ultrasonic waves, or ultrasonic wave pulses (or a plurality of such pulses) at one or more of a selected repetition rate, a selected pulse duration, a selected duty cycle, a selected peak power, a selected average pulse power, or a selected total duration. The parameters of the ultrasonic waves generated by the transducers are selected to apply a mixing and suspending force in the liquid held by the container such that single cells are dissociated from the tissue, but to minimize cell lysis.

In some embodiments, the control module operates the transducer to generate one or more ultrasonic wave pulses. The ultrasonic wave pulses may be generated at a selected repetition rate, which can be controlled, for example, by the repetition rate of the RF energy applied to the transducer. For example, the repetition rate may be about 1 Hz to about 100,000 Hz (such as about 1 Hz to about 5 Hz, about 5 Hz to about 10 Hz about 10 Hz to about 25 Hz, about 25 Hz to about 50 Hz, about 50 Hz to about 100 Hz, about 100 Hz to about 150 Hz, about 150 Hz to about 200 Hz, about 200 Hz to about 300 Hz, about 300 Hz to about 400 Hz, about 400 Hz to about 500 Hz, about 500 Hz to about 750 Hz, or about 750 Hz to about 1000 Hz, about 1000 Hz to about 2500 Hz, about 2500 Hz to about 5000 Hz, about 5000 Hz to about 10,000 Hz, about 10,000 Hz to about 25,000 Hz, about 25,000 Hz to about 50,000 Hz, or about 50,000 Hz to about 100,000 Hz). The repetition rate refers to the frequency of the ultrasonic wave pulses when the transducer is operated to emit a plurality of ultrasonic wave pulses. In some embodiments, the ultrasonic wave pulses are generated at a duty cycle of about 0.1% to about 95% (such as about 0.1% to about 0.25%, about 0.25% to about 0.5%, about 0.5% to about 1%, about 1% to about 2%, about 2% to about 3%, about 3% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 95%).

If the ultrasonic energy is applied to the sample container for too long of a time period, the cells within the sample container may lyse. Accordingly, the control module is configured to operate the transducer to generate the ultrasonic waves (or wave pulses) for selected duration of time, for example between about 2 seconds and about 90 minutes (for example about 2 seconds to about 5 seconds, about 5 seconds to about 10 seconds, about 10 seconds to about 15 seconds, about 15 seconds to about 30 seconds, about 30 seconds to about 1 minutes, about 1 minute to about 2 minutes, about 2 minutes to about 4 minutes, about 4 minutes to about 6 minutes, about 6 minutes to about 8 minutes, about 8 minutes to about 10 minutes, about 10 minutes to about 15 minutes, about 15 minutes to about 30 minutes, about 30 minutes to about 45 minutes, about 45 minutes to about 60 minutes, about 60 minutes to about 75 minutes, or about 75 minutes to about 90 minutes).

In certain embodiment, the system is configured to control the temperature of the biological tissue sample using a coupling medium, energy from the ultrasonic wave pulses, or both. As discussed above, the ultrasonic wave pulses can be configured to apply energy to the biological sample to heat the sample, or a portion of the ultrasonic waves used to apply energy to the biological tissue sample is configured to heath the sample. A coupling medium may be use (alternatively or additionally) to control the temperature of the biological tissue sample. The coupling medium is thermally coupled to the biological tissue sample, and controlling the temperature of the coupling medium can control the temperature of the biological tissue sample. For example, the coupling medium may be chilled, which can be used to bring down the temperature of the biological tissue sample. In some embodiments, the temperature of the biological tissue sample is heated using one or more ultrasonic wave pulses configured to heat the biological tissue sample for a period of time, and the coupling fluid may be used to decrease the temperature of the biological tissue sample after the biological tissue sample was heated. This allows for heat to be controllably applied to the biological tissue sample for a relatively short period of time, which may help dissociate single cells from the tissue, but the temperature of the biological tissue sample may then be brought down using the coupling medium so that the cells limit expression of pro-inflammatory and/or stress induced genes.

The coupling medium of the system couples the one or more FASA elements of the transducer to the sample container. Energy from the ultrasonic waves generated by the transducer can be transmitted into the sample container through the coupling fluid, which then dissociates single cells from the biological tissue sample within the sample container. The coupling medium may be a fluid (e.g., a liquid), a solid, or a gel. Exemplary coupling media can include, but are not limited to, water, a buffer, an oil, a water-based gel, propylene glycol, glycerin, or glycol ether.

The system may include a temperature controller configured to control the temperature of the coupling medium. As the coupling medium can be thermally coupled to the sample container, the temperature of the sample within the sample container can be controlled by controlling the temperature of the coupling fluid. If the temperature of the sample container gets too warm, the cells may lyse or otherwise become non-viable. However, too cool of a temperature can also make the cells non-viable. In some embodiments, the coupling medium is controlled at a temperature of about 2° C. to about 70° C. (such as between about 2° C. and about 5° C., between about 5° C. and about 10° C., between about 10° C. and about 15° C., between about 15° C. and about 25° C., between about 25° C. and about 35° C., between about 35° C. and about 45° C., between about 45° C. and about 55° C., or between about 55° C. and about 70° C.). In some embodiments, the peak temperature of the sample during cell dissociation is about 2° C. to about 80° C. (such as about 4° C. to about 10° C., about 10° C. to about 15° C., about 15° C. to about 25° C., about 25° C. to about 35° C., about 35° C. to about 45° C., about 45° C. to about 55° C., about 55° C. to about 65° C., or about 65° C. to about 80° C.). In some embodiments, the temperature of the sample increases by less than about 50° C., less than about 40° C., less than about 30° C., less than about 20° C., less than about 15° C., less than about 10° C., or less than about 5° C. during dissociation of the cells from the tissue sample. The system may be further configured with a pump, which can circulate the coupling medium between a position between the transducer and the sample container, and the temperature controller.

Figure 5:
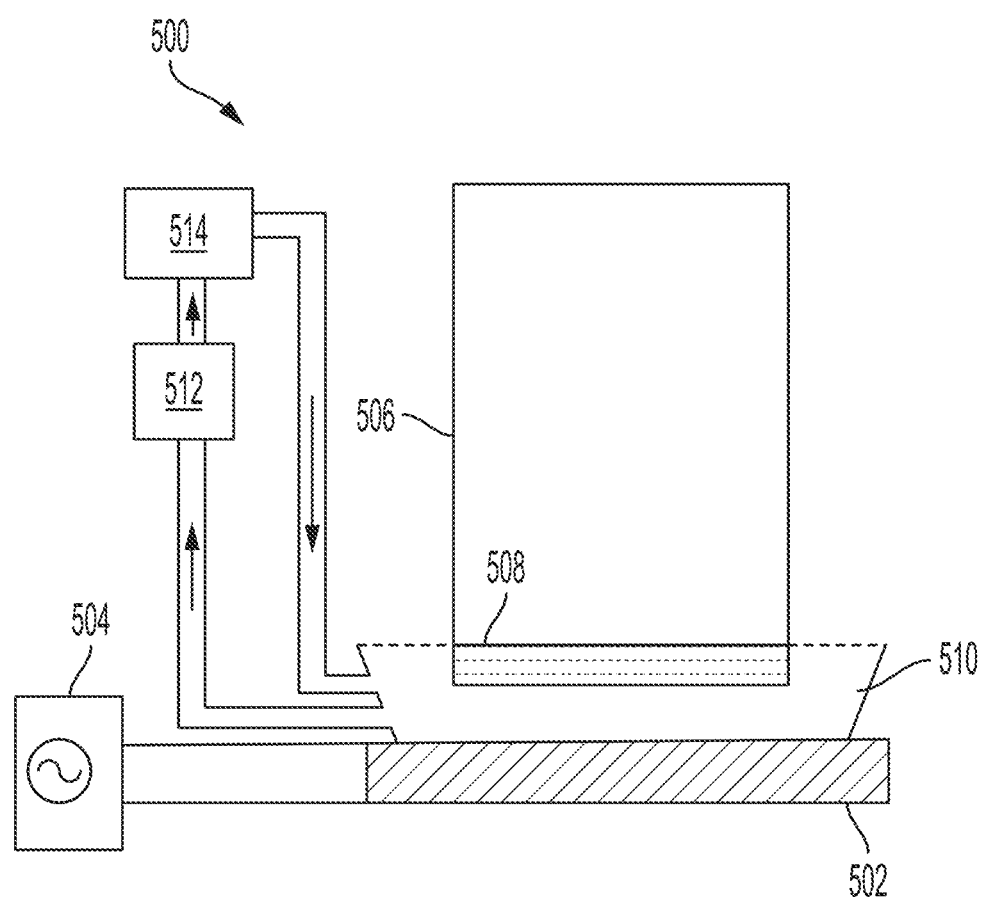
FIG. 5 shows an exemplary system with a temperature controller and pump configured to control the temperature of the coupling fluid when the transducer is in operation.

FIG. 5 illustrates an exemplary system with a temperature controller and pump configured to control the temperature of the coupling fluid when the transducer is in operation. In FIG. 5, system 500 includes a transducer 502 with one or more FASA elements configured to generate ultrasonic wave directed to a sample container 506 coupled to the transducer by a coupling medium 510. The transducer is operated using a control module 504, which can selectively pass an electrical current through the one or more FASA elements to generate the ultrasonic waves. The sample container 506 is configured to hold a biological tissue sample 508. The coupling medium 510 is fluidly connected to a pump 512 and a temperature controller 514. During operation of the system 500, the coupling medium 510 can be circulated using the pump 512 to the temperature controller 514, which can operate to warm or cool the coupling medium 510. Because the coupling medium 510 is thermally coupled to the sample container 506, the temperature controller can indirectly modulate the temperature of the biological tissue sample within the sample container.

The sample container may be a sample tube, well, or other suitable container configured to hold a desired amount of liquid and/or biological tissue sample. For example, the sample container may be a standard laboratory tube, which may be made from a plastic, such as polystyrene or polypropylene, or any other suitable material. In some embodiments, the sample container is disposed within a sample tube array, for example a well within a multi-well plate (e.g., a 6-well plate, a 12-well plate, a 24-well plate, a 48-well plate, a 96-well plate, or a 384-well plate). A multi-well plate may be used, for example, with a transducer array as discussed above.

The device described above may be used with any of the methods described herein.

Methods of Dissociating Single Cells from a Biological Tissue Sample

Single cells can be dissociated from a biological tissue sample by applying energy from one or more ultrasonic wave pulses to a sample container holding the biological tissue sample. The ultrasonic wave pulses can be generated using a transducer configured with one or more Fresnel Annular Sector Actuator (FASA) elements, which can direct the lateral ultrasonic energy in the direction of the sample container through a coupling medium. The coupling medium couples the FASA elements to the sample container, and transmits energy from the ultrasonic waves generated by the transducer to the sample container. The energy applied to the sample container applies a mixing and/or suspending force to the sample, which causes single cells to dissociate from the biological tissue sample. In some embodiments, the method further includes controlling the temperature of the biological tissue sample while energy form the one or more generated ultrasonic wave pulses is applied to the biological tissue sample in the sample container.

In some embodiments, the temperature of the biological tissue sample is controlled by using a coupling medium, energy from the ultrasonic wave pulses, or both. As discuss above, the ultrasonic waves can be figured to apply a heating energy to the biological tissue sample, which can increase the temperature of the biological tissue sample in the container. Temperate increase for a controlled period of time may increase the dissociation of single cells from the biological tissue sample, although prolonged heating can result in inducing one or more pro-inflammatory or stress-associated gene expression. Exemplary pro-inflammatory or stress associate genes that may be expressed upon prolonged heat exposure include, but are not limited to CD69, LRRK2, TNF, FOS, PDE4B, NR4A3, S100A9, S100A8, THBD, IL-1β, IL-1α, HK2, CXCL8, CXCL1, AREG, ERG2, TIMP1, and CXCR4.

In some embodiments, the temperature of the biological tissue sample is controlled to between about 2° C. to about 70° C. (such as between about 2° C. and about 5° C., between about 5° C. and about 10° C., between about 10° C. and about 15° C., between about 15° C. and about 25° C., between about 25° C. and about 35° C., between about 35° C. and about 45° C., between about 45° C. and about 55° C., or between about 55° C. and about 70° C.).

The biological tissue sample may be thermally coupled to the coupling medium such that controlling the temperature of the coupling medium can control the temperature of the biological tissue sample. For example, the coupling medium may be cooled to decrease the temperature of the biological tissue sample. Cooling the biological tissue sample through the coupling medium can, for example, reduce the temperature of the sample after being heated using ultrasonic waves configured to apply heating energy to the sample. In some embodiments, the coupling medium is warmed to increase the temperature of the biological tissue sample. The temperature of the coupling medium may be controlled, for example between about 2° C. to about 70° C. (such as between about 2° C. and about 5° C., between about 5° C. and about 10° C., between about 10° C. and about 15° C., between about 15° C. and about 25° C., between about 25° C. and about 35° C., between about 35° C. and about 45° C., between about 45° C. and about 55° C., or between about 55° C. and about 70° C.). For example, the coupling medium may be liquid or gel held in a temperature controlled compartment, or the coupling medium may be cycled through a temperature controller. The coupling medium may be thermally coupled to the sample container (and thus, the biological tissue sample within the sample chamber). Therefore, by controlling the temperature of the coupling medium, the temperature of the biological tissue sample itself can be controlled. In some embodiments, the one or more ultrasonic wave pulses are configured to apply a heating energy to the biological tissue sample, which can be applied to control the temperature of the biological tissue sample. In some embodiments, the energy from the ultrasonic waves does not apply a heating energy to the biological tissue sample. The energy from the ultrasonic waves applied to the biological tissue sample may be heterogeneous during the cell dissociation process. For example, a first portion of the ultrasonic waves may apply a heating energy to the biological tissue sample, and a second portion of the ultrasonic waves does not apply a heating energy to the biological tissue sample. The biological tissue sample may be heated using the ultrasonic waves, and then cooled, for example by the coupling medium, to limit the expression of pro-inflammatory and/or stressed induces genes. In some embodiments, the biological tissue sample is heated to a peak temperature between about 20° C. and about 70° C. (such as between about 20° C. and about 25° C., between about 25° C. and about 35° C., between about 35° C. and about 45° C., between about 45° C. and about 55° C., or between about 55° C. and about 70° C.).

The ultrasonic waves emitted by the transducer may be emitted in one or more ultrasonic wave pulses. In some embodiments, a plurality of ultrasonic wave pulses are emitted by the transducer. The plurality of ultrasonic wave pulses may be generated, for example, at a repetition rate of 1 Hz to about 100,000 Hz (such as about 1 Hz to about 5 Hz, about 5 Hz to about 10 Hz about 10 Hz to about 25 Hz, about 25 Hz to about 50 Hz, about 50 Hz to about 100 Hz, about 100 Hz to about 150 Hz, about 150 Hz to about 200 Hz, about 200 Hz to about 300 Hz, about 300 Hz to about 400 Hz, about 400 Hz to about 500 Hz, about 500 Hz to about 750 Hz, or about 750 Hz to about 1000 Hz, about 1000 Hz to about 2500 Hz, about 2500 Hz to about 5000 Hz, about 5000 Hz to about 10,000 Hz, about 10,000 Hz to about 25,000 Hz, about 25,000 Hz to about 50,000 Hz, or about 50,000 Hz to about 100,000 Hz). The ultrasonic wave pulses have a lateral force, which allows for dissociation of single cells from the biological tissue.

In some embodiments, the one or more ultrasonic wave pulses are generated at a duty cycle of about 0.1% to about 95% (such as about 0.1% to about 0.25%, about 0.25% to about 0.5%, about 0.5% to about 1%, about 1% to about 2%, about 2% to about 3%, about 3% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 95%).

In some embodiments, energy from the one or more ultrasonic wave pulses is applied to the coupling medium for about 2 seconds to about 90 minutes (for example about 2 seconds to about 5 seconds, about 5 seconds to about 10 seconds, about 10 seconds to about 15 seconds, about 15 seconds to about 30 seconds, about 30 seconds to about 1 minutes, about 1 minute to about 2 minutes, about 2 minutes to about 4 minutes, about 4 minutes to about 6 minutes, about 6 minutes to about 8 minutes, about 8 minutes to about 10 minutes, about 10 minutes to about 15 minutes, about 15 minutes to about 30 minutes, about 30 minutes to about 45 minutes, about 45 minutes to about 60 minutes, about 60 minutes to about 75 minutes, or about 75 minutes to about 90 minutes).

The single cells are efficiently dissociated from the biological tissue sample, and a substantial portion of the single cells remain viable after dissociation. The methods provided herein are thorough enough to dissociate the single cells, but are gentle enough to limit cell lysis. For example, in some embodiments, about 20% or more, about 30% or more, about 40% or more, about 50% or more, about 60% or more, about 70% or more, about 80% or more, or about 90% or more of the single cells dissociated from the tissue remain viable after dissociation from the biological tissue sample. In some embodiments, about 20% to about 95% (such as about 20% to about 30%, about 30% to about 40%, about 40% to about 50%, about 50% to about 60%, about 60% to about 70%, about 70% to about 80%, about 80% to about 90%, or about 90% to about 95%) of the cells dissociated from the tissue remain viable after dissociation from the biological tissue sample.

The biological tissue sample may be a solid tissue sample, although the solid tissue sample may be minced into clusters of adhered cells before single cells are dissociated from the biological tissue sample. A blender, scalpel, scissors, or other suitable device may be used to mince the cells, although care should be taken to avoid cell lysis. The tissue may be minced, for example, to a size of about 0.25 $mm^3$ to about 5 $mm^3$ (for example, about 0.25 $mm^3$ to about 0.5 $mm^3$, about 0.5 $mm^3$ to about 1 $mm^3$, about 1 $mm^3$ to about 2 $mm^3$, about 2 $mm^3$ to about 3 $mm^3$, about 3 $mm^3$ to about 4 $mm^3$, or about 4 $mm^3$ to about 5 $mm^3$. In some embodiments, the biological tissue sample is suspended in a liquid within the sample container, such as water, a buffer, or other suitable liquid medium (for example, Roswell Park Memorial Institute (RPMI) medium, Minimum Essential Medium (MEM), Iscove's Modified Dulbecco's Medium (IMDM), or Dulbecco's Modified Eagle Medium (DMEM).

Cells bind to each other in tissue through cell adhesion molecules, such as integrins, IgSF CAMs, cadherins, and selectins, which can form cell junctions. Although cell adhesion molecules can be enzymatically degraded, for example using a protease (such as trypsin, collagenase, and/or dispase). However, treatment of cells with such enzymes can depress cell viability, as the proteases can cleave unintended proteins. The methods described herein can effectively dissociate single cells from the biological tissue sample without the use of non-endogenous proteases (the tissue may naturally include one or more proteases, but such endogenous proteases are generally ineffective at dissociating single viable cells from tissue). In some embodiments, the biological tissue sample is substantially free or free of non-endogenous proteases. In this context, "substantially free" of a non-endogenous protease is understood to mean that small amounts of non-endogenous protease may be present so long as such non-endogenous protease does not affect the proportion single, viable cells that dissociate from the biological tissue sample.

In some embodiments, the biological tissue sample is an animal tissue, and may be, for example vertebrate or invertebrate tissue. For example, the tissue may be, but is not limited to, mammalian, reptilian, avian, fish, insect, or nematode tissue. In some embodiments, the tissue is a plant tissue. In some embodiments, the tissue contains eukaryotic cells. In some embodiments, the cells are multicellular prokaryotes (e.g., a biofilm). In some embodiments, the tissue is a tumor tissue or a cancer tissue, or a biopsy sample. The biological tissue sample may be, for example, a lung, kidney, liver, pancreas, stomach, brain, skin, intestine, muscle, breast, splenic, bladder, uterine, ovarian, prostate, cardiac, bone marrow, or any other solid tissue, which may be a diseased tissue or a healthy tissue, such as cancerous tissue or non-cancerous tissue. The cells dissociated from the tissue sample may include two or more different types of viable cells. The tissue sample may be a heterogeneous tissue sample, and the different cell types may be dissociated from the tissue sample. For example, a cancer tissue sample may include multiple different cell types, such as macrophages, T cells, natural killer (NK) cells, and cancer cells, one or more of which may be dissociated from the tissue sample.

Exemplary Embodiments

The following embodiments are exemplary and are not intended to limit the scope of the invention(s) described herein. One skilled in the art can would understand that the exemplary embodiments may be modified by adding or excluding one or more features from the exemplary embodiments.

Embodiment 1. A method of dissociating single cells from a biological tissue sample, comprising:
 generating one or more ultrasonic wave pulses using a transducer comprising one or more Fresnel Annular Sector Actuator (FASA) elements; and
 applying energy from the one or more generated ultrasonic wave pulses to a biological tissue sample contained by a sample container through a coupling medium that couples the one or more FASA elements to the sample container to dissociate single cells from the biological tissue.

Embodiment 2. A method of dissociating single cells from a biological tissue sample, comprising:
 generating one or more ultrasonic wave pulses using a transducer comprising one or more Fresnel Annular Sector Actuator (FASA) elements;
 applying energy from the one or more generated ultrasonic wave pulses to a biological tissue sample contained by a sample container through a coupling medium that couples the one or more FASA elements to the sample container to dissociate single cells from the biological tissue; and
 controlling the temperature of the biological tissue sample while the energy from the one or more generated ultrasonic wave pulses is applied to the biological tissue sample.

Embodiment 3. The method of embodiment 2, wherein controlling the temperature of the biological tissue sample comprises controlling the temperature of the coupling medium.

Embodiment 4. The method of embodiment 3, wherein the temperature of the coupling medium is controlled to cool the biological tissue sample or limit a temperature increase of the biological tissue sample.

Embodiment 5. The method of embodiment 3 or 4, wherein the coupling medium is controlled to a temperature between about 2° C. and about 70° C.

Embodiment 6. The method of any one of embodiments 3-5, wherein the coupling medium is controlled to a temperature between about 2° C. and about 25° C.

Embodiment 7. The method of any one of embodiments 2-6, wherein controlling the temperature of the biological tissue sample comprises heating the biological tissue sample using the energy from the one or more generated ultrasonic wave pulses.

Embodiment 8. The method of embodiment 7, wherein a first portion of the one or more ultrasonic wave pulses generated by the transducer are configured to heat the biological tissue sample and a second portion of the one or more ultrasonic wave pulses generated by the transducer are configured to not heat the biological tissue sample.

Embodiment 9. The method of embodiment 7 or 8, wherein the biological tissue sample is heated to a peak temperature between about 20° C. and about 70° C.

Embodiment 10. The method of any one of embodiments 1-6, wherein the biological tissue sample is heated by less than 15° C. or is not heated during the application of energy from the one or more generated ultrasonic wave pulses to the sample container.

Embodiment 11. The method of any one of embodiments 2-10, wherein the temperature of the biological tissue sample is controlled to between about 2° C. and about 70° C.

Embodiment 12. The method of any one of embodiments 2-11, wherein controlling the temperature of the biological tissue sample reduces the expression of one or more pro-inflammatory or stressed-induced genes compared to not controlling the temperature of the biological tissue sample.

Embodiment 13. The method of embodiment 12, wherein the one or more pro-inflammatory or stressed-induced genes is selected from the group consisting of CD69, LRRK2, TNF, FOS, PDE4B, NR4A3, S100A9, S100A8, THBD, IL-1β, IL-1α, HK2, CXCL8, CXCL1, AREG, ERG2, TIMP1, and CXCR4.

Embodiment 14. The method of any one of embodiment 1-13, wherein the coupling medium is a liquid, a solid, or a gel.

Embodiment 15. The method of embodiment 1-14, wherein the coupling medium is a liquid, the method further comprising cycling the coupling fluid through a temperature controller.

Embodiment 16. The method of any one of embodiments 1-15, wherein about 20% or more of the dissociated single cells are viable.

Embodiment 17. The method of embodiment 16, wherein about 20% to about 95% of the dissociated single cells are viable.

Embodiment 18. The method of any one of embodiments 1-17, wherein two or more different types of viable cells are dissociated from the biological tissue sample.

Embodiment 19. The method of any one of embodiments 1-18, wherein the biological tissue sample comprises a cancer tissue.

Embodiment 20. The method of any one of embodiments 1-19, wherein the energy applied to the sample does not result in a shear force applied to the sample.

Embodiment 21. The method of any one of embodiments 1-20, comprising selecting one or more of a repetition rate, a pulse duration, a duty cycle, a peak power, or a total duration for the one or more generated ultrasonic wave pulses.

Embodiment 22. The method of any one of embodiments 1-21, wherein the energy applied to the sample results in a mixing force or a suspending force applied to the sample.

Embodiment 23. The method of any one of embodiments 1-22, wherein a plurality of ultrasonic wave pulses are generated at a repetition rate of about 1 Hz to about 100,000 Hz.

Embodiment 24. The method of any one of embodiments 1-23, wherein the one or more ultrasonic wave pulses are generated at a duty cycle of about 0.1% to about 95%.

Embodiment 25. The method of any one of embodiments 1-24, wherein energy from the one or more ultrasonic wave pulses is applied to the coupling medium for about 2 seconds to about 90 minutes.

Embodiment 26. The method of any one of embodiments 1-25, wherein the biological tissue is suspended in a liquid within the sample container.

Embodiment 27. The method of any one of embodiments 1-26, wherein the biological tissue is minced.

Embodiment 28. The method of any one of claims 1-27, wherein the biological tissue sample is substantially free of non-endogenous proteases.

Embodiment 29. The method of any one of embodiments 1-28, wherein the transducer comprises four or more FASA elements.

Embodiment 30. The method of any one of embodiments 1-29, wherein the biological tissue sample is an unpreserved sample.

Embodiment 31. A system for dissociating single cells from a biological tissue sample, comprising:
 a transducer comprising one or more Fresnel Annular Sector Actuator (FASA) elements configured to generate one or more ultrasonic wave pulses;
 a sample container configured to hold the biological tissue sample; and
 a coupling medium configured to couple the one or more FASA elements to the sample container and transmit energy from the plurality of ultrasonic wave pulses generated by the transducer to the sample container to dissociate single cells from the biological tissue sample.

Embodiment 32. A system for dissociating single cells from a biological tissue sample, comprising:
 a transducer comprising one or more Fresnel Annular Sector Actuator (FASA) elements configured to generate one or more ultrasonic wave pulses;
 a sample container configured to hold the biological tissue sample, wherein the system is configured to control the temperature of the biological tissue sample; and
 a coupling medium configured to couple the one or more FASA elements to the sample container and transmit energy from the plurality of ultrasonic wave pulses generated by the transducer to the sample container to dissociate single cells from the biological tissue sample.

Embodiment 33. The system of embodiment 32, wherein the system is configured to control the temperature of the biological sample to a temperature between about 2° C. and about 70° C.

Embodiment 34. The system of any one of embodiments 31-33, further comprising a temperature controller configured to control the temperature of the coupling medium.

Embodiment 35. The system of embodiment 34, wherein the temperature controller is configured to control the coupling medium to a temperature between about 2° C. and about 70° C.

Embodiment 36. The system of embodiment 34, wherein the temperature control is configured to cool the coupling medium to a temperature between about 2° C. and about 25° C.

Embodiment 37. The system of any one of embodiments 31-36, wherein the coupling medium is a liquid, the system further comprising a pump configured to circulate the coupling medium between a position between the transducer and the sample container, and the temperature controller.

Embodiment 38. The system of any one of embodiments 32-37, wherein the system is configured to control the temperature of the biological tissue sample by heating the biological tissue sample using energy from the one or more generated ultrasonic wave pulses.

Embodiment 39. The system of any one of embodiments 32-38, wherein the transducer is configured selectively generate (1) one or more ultrasonic wave pulses that heat the biological tissue sample and (2) one or more ultrasonic wave pulses that do not heat the sample.

Embodiment 40. The system of any one of embodiments 31-39, further comprising a control module configured to operate the transducer to generate the one or more ultrasonic wave pulses.

Embodiment 41. The system of embodiment 40, wherein the control module is configured to operate the transducer to generate the plurality of ultrasonic wave pulses at one or more of a selected repetition rate, a selected pulse duration, a selected duty cycle, a selected peak power, a selected average pulse power, or a selected total duration.

Embodiment 42. The system of embodiment 40 or 41, wherein the control module is configured to operate the transducer to generate a plurality of ultrasonic wave pulses at a repetition rate of about 1 Hz to about 100,000 Hz.

Embodiment 43. The system of any one of embodiments 40-42, wherein the control module is configured to operate the transducer to generate the one or more ultrasonic wave pulses at a duty cycle of about 0.1% to about 95%.

Embodiment 44. The system of any one of embodiments 40-43, wherein the control module is configured to operate the transducer to generate the one or more ultrasonic wave pulses for a total duration of about 2 seconds to about 90 minutes.

Embodiment 45. The system of any one of embodiments 40-44, wherein the control module comprises a radio-frequency (RF) generator configured to operate the transducer to generate the ultrasonic wave pulses.

Embodiment 46. The system of any one of embodiments 40-45, wherein the control module is configured to operate the transducer to generate the one or more ultrasonic wave pulses so that a shear force is not applied to the sample.

Embodiment 47. The system of any one of embodiments 40-46, wherein the control module is configured to operate the transducer to generate the one or more ultrasonic wave pulses so that a mixing force or a suspending force is applied to the sample.

Embodiment 48. The system of any one of embodiments 30-47, wherein the transducer comprises four or more FASA elements.

Embodiment 49. The system of any one of embodiments 30-48, wherein the system is disposed in an array comprising a plurality of systems.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1

Three tissue samples were prepared by adding approximately 100 mg of liver tissue to a petri dish to which 250 μL Rosewell Park Memorial Institute (RPMI) medium was added. The liver tissue sample was minced to tissue pieces about 1 mm$^3$ to about 3 mm$^3$ in size. Tissue sample was transferred to a sample tube. The sample tube was positioned over a transducer with 4 independently operable FASA elements having a 90° angle arranged in a circular pattern having a diameter of approximately 9 mm. water bath (i.e., coupling fluid) controlled the sample temperature by setting a chiller to 25° C. The FASA elements were activated by applying RF energy to the FASA elements so that bulk lateral ultrasonic (BLU) energy is applied to the sample. Three of the four FASA elements were activated at any given time point, within the inactive FASA element rotating clockwise.

After applying the ultrasonic waves to the samples, the samples were passed through a 70 μm cell strainer, and 10 μL of the filtrate was visualized under a microscope. The high ultrasonic wave pulse frequency and a prolonged duration of the application of the ultrasonic waves resulted in cell lysis. Lower pulse frequency at a shorter duration, however, resulted in viable cells.

Example 2

A liver tissue sample was prepared by adding approximately 100 mg of liver tissue to a petri dish to which 250 μL Rosewell Park Memorial Institute (RPMI) medium was added. The liver tissue sample was minced to tissue pieces about 1 mm$^3$ to about 3 mm$^3$ in size. Tissue sample was transferred to a sample tube. The sample tube was then positioned over a transducer with 4 independently operable FASA elements having a 90° angle arranged in a circular pattern having a diameter of approximately 9 mm. A water bath (i.e., coupling fluid) controlled the sample temperature by setting a chiller to 25° C. The FASA elements were activated by applying RF energy to the FASA elements so that apply bulk lateral ultrasonic (BLU) energy was applied to the sample. Three of the four FASA elements were activated at any given time point, within the inactive FASA element rotating clockwise.

Control samples (from liver tissue) were also prepared by enzymatic dissociation methods at 37° C.

The samples were separately transferred to a 15 mL centrifuge tube and topped with 5 mL of wash buffer (1% bovine serum albumin (BSA) in phosphate buffered saline (PBS)). The centrifuge tubes were centrifuged at 300×g for 5 minutes at 4° C., and the supernatant was decanted. The pellet was re-suspended in 1 mL wash buffer using a wide-orifice 1 mL pipette tip before adding 5 mL ACK (Ammonium-Chloride Potassium) lysing buffer and allowing the cells to incubate at room temperature for 5-7 minutes. 5 mL of stop-reaction buffer (1% BSA in Dulbecco's Phosphate-Buffered Saline (DPBS) (Ca$^{2+}$ and Mg$^{2+}$ free)) was added to the samples, which were then centrifuged at 300×g for 5 minutes at 4° C. The supernatant was then removed, and the resulting pellet was suspended in 5 mL DPBS. The suspended cells were filtered using a 70 μm cell strainer and the filtrate topped to 5 mL using additional DPBS. The suspended cells were mixed, and a 600 μL sample was used to determine cell viability using a Vi-CELL cell viability analyzer. Results are shown in Table 1.

TABLE 1

|  | Test Sample | Enzymatic Control 1 | Enzymatic Control 2 |
|---|---|---|---|
| Total cells/mL (×10^6) | 0.13 | 0.14 | 0.04 |
| Viable cells/mL (×10^6) | 0.098 | 0.11 | 0.02 |
| Viability % | 77.5 | 76.1 | 57.9 |
| Viable cells per mg tissue | 9,800 | 11,000 | 2,000 |
| Total cells per mg tissue | 13,000 | 14,000 | 4,000 |

Approximately 77.5% of the cells dissociated from the liver tissue using ultrasonic waves (the Test Sample) were viable in a yield of approximately 9,800 viable cells per mg of liver tissue.

Example 3

Seven liver tissue samples (Sample Nos. 1-7) and seven kidney samples (Samples 8-14) were prepared by adding approximately 100 mg of liver tissue or kidney tissue to a petri dish, to which 200 μL Rosewell Park Memorial Institute (RPMI) medium was added. The liver tissue samples were minced to tissue pieces about 1 mm$^3$ to about 3 mm$^3$ in size using scissors or a scalpel. 200 μL of the minced tissue sample was transferred to a sterile sample tube. The sample tube was then positioned over a transducer with 4 independently operable FASA elements having a 90° angle arranged in a circular pattern having a diameter of approximately 9 mm. A water bath (i.e., coupling fluid) controlled the sample temperature by setting a chiller to 22° C. (resulting in a 25° C. water bath). The FASA elements were activated by applying RF energy to the FASA elements so that apply bulk lateral ultrasonic (BLU) energy was applied to the sample. Three of the four FASA elements were activated at any given time point, within the inactive FASA element rotating clockwise. Peak sample temperature was measured during the application of the ultrasonic energy, as shown in Table 2.

TABLE 2

| Sample No. | Viable cells per mg tissue | Peak Sample Temperature (° C.) |
|---|---|---|
| 1 | ~6,500 | 50 |
| 2 | ~8,547 | 47 |
| 3 | ~5,909 | 37 |
| 4 | ~10,000 | 33 |
| 5 | ~7,758 | 47 |
| 6 | ~17,222 | 71 |
| 7 | ~13,043 | 65 |
| 8 | ~332,211 | 50 |
| 9 | ~280,701 | 47 |
| 10 | ~444,500 | 37 |
| 11 | ~307,292 | 33 |
| 12 | ~255,803 | 47 |
| 13 | ~287,857 | 71 |
| 14 | ~175,000 | 65 |

The samples were separately transferred to a 15 mL centrifuge tube and topped with 5 mL of wash buffer (1% bovine serum albumin (BSA) in phosphate buffered saline (PBS)). The centrifuge tubes were centrifuged at 300×g for 5 minutes at 4° C., and the supernatant was decanted. The pellet was re-suspended in 1 mL wash buffer using a wide-orifice 1 mL pipette tip before adding 5 mL ACK (Ammonium-Chloride Potassium) lysing buffer and allowing the cells to incubate at room temperature for 5-7 minutes. 5 mL of stop-reaction buffer (1% BSA in Dulbecco's Phosphate-Buffered Saline (DPBS) ($Ca^{2+}$ and $Mg^{2+}$ free)) was added to the samples, which were then centrifuged at 300×g for 5 minutes at 4° C. The supernatant was then removed, and the resulting pellet was suspended in 5 mL DPBS. The suspended cells were filtered using a 70 μm cell strainer and the filtrate topped to 5 mL using additional DPBS. The suspended cells were mixed, and a 600 μL sample was used to determine cell viability using a Vi-CELL cell viability analyzer. Results are shown in Table 2.

Example 4

Approximately 100 mg of rabbit splenic tissue was placed in a petri dish, to which Rosewell Park Memorial Institute (RPMI) medium was added. The splenic tissue sample was minced to tissue pieces about 1 $mm^3$ to about 3 $mm^3$ in size. The minced tissue sample was transferred to a sterile sample tube. The sample tube was then positioned over a transducer with 4 independently operable FASA elements having a 90° angle arranged in a circular pattern having a diameter of approximately 9 mm. Bulk lateral ultrasonic energy was applied to the sample to dissociate cells from the minced splenic tissue.

Separately, cells form a rabbit splenic tissue were dissociated using an enzymatic dissociation for 45 minutes.

The samples were separately transferred to a 15 mL centrifuge tube and topped with 5 mL of wash buffer (1% bovine serum albumin (BSA) in phosphate buffered saline (PBS)). The centrifuge tubes were centrifuged at 300×g for 5 minutes at 4° C., and the supernatant was decanted. The pellet was re-suspended in 1 mL wash buffer using a wide-orifice 1 mL pipette tip before adding 5 mL ACK (Ammonium-Chloride Potassium) lysing buffer and allowing the cells to incubate at room temperature for 5-7 minutes. 5 mL of stop-reaction buffer (1% BSA in Dulbecco's Phosphate-Buffered Saline (DPBS) ($Ca^{2+}$ and $Mg^{2+}$ free)) was added to the samples, which were then centrifuged at 300×g for 5 minutes at 4° C. The supernatant was then removed, and the resulting pellet was suspended in 5 mL DPBS. The suspended cells were filtered using a 70 μm cell strainer and the filtrate topped to 5 mL using additional DPBS.

Figure 6A:
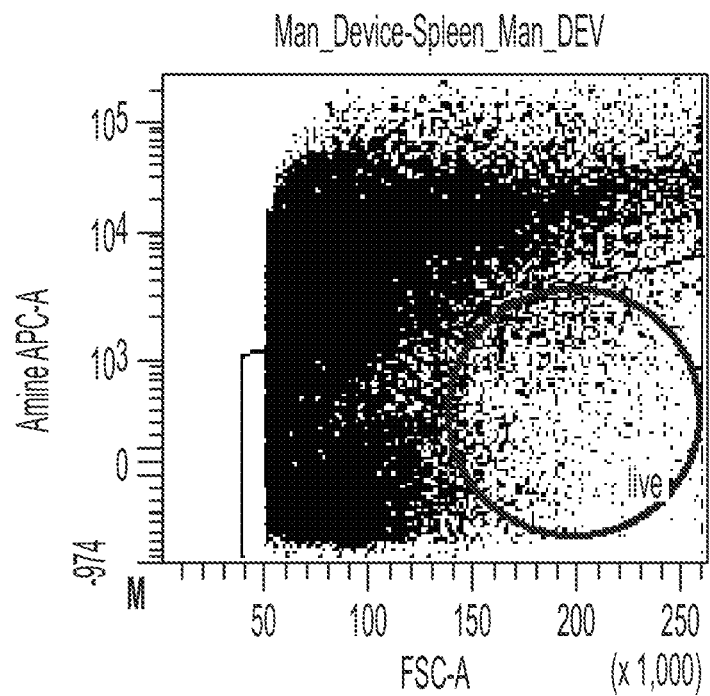
FIG. 6A shows the results of flow cytometry analysis from cells dissociated from a rabbit splenic tissue sample using an enzymatic dissociation method to distinguish between living and dead dissociated cells.
Figure 6B:
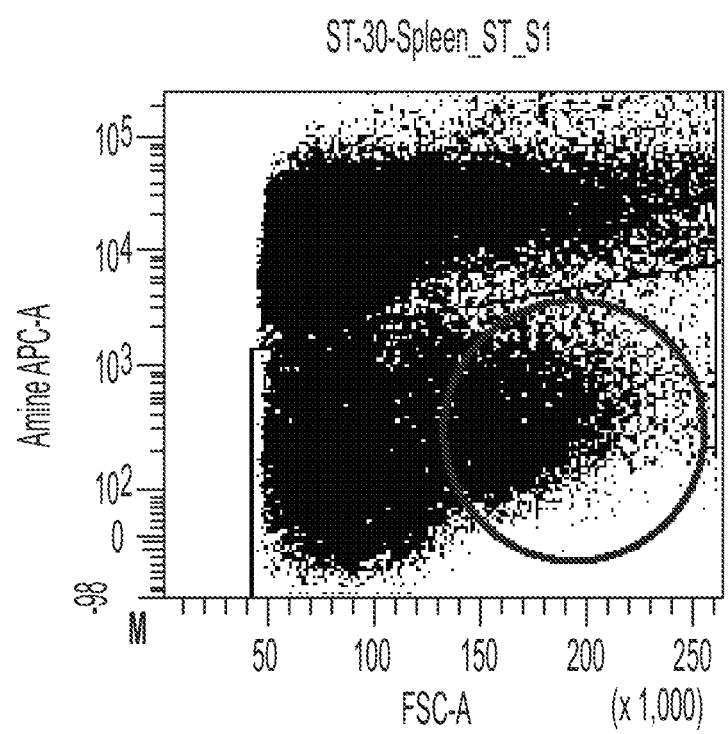
FIG. 6B shows the results of flow cytometry analysis from cells dissociated from a rabbit splenic tissue sample using bulk lateral ultrasonic energy as described herein to distinguish between living and dead dissociated cells.
Figure 6C:
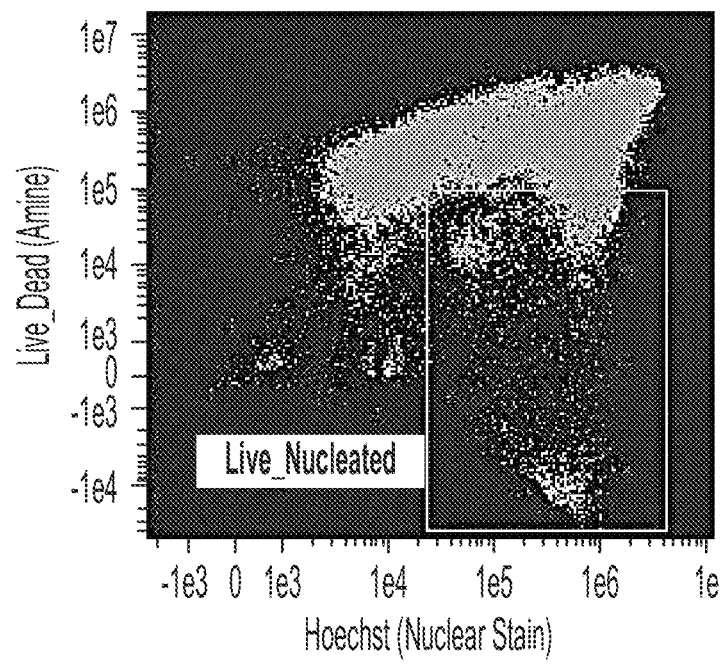
FIG. 6C shows the results of flow cytometry analysis from cells dissociated from a rabbit splenic tissue sample using an enzymatic dissociation method to distinguish between nucleated, living cells from other cell debris.
Figure 6D:
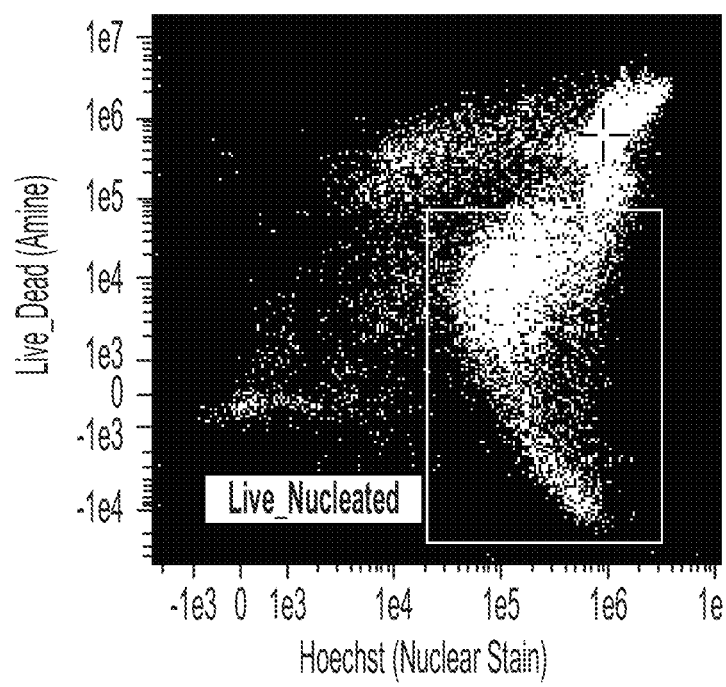
FIG. 6D shows the results of flow cytometry analysis from cells dissociated from a rabbit splenic tissue sample using bulk lateral ultrasonic energy as described herein to distinguish between nucleated, living cells from other cell debris.

Cells from the rabbit splenic tissue dissociated using bulk lateral ultrasonic waves and cells dissociated using the enzymatic methods were compared using flow cytometry (FACS). Results are shown in FIG. 6A-6D. FIGS. 6A and 6B compare the cell population diversity, showing that dissociating cells using bulk lateral ultrasonic waves (FIG. 6B) results in a greater cell diversity compared to enzymatic dissociation (FIG. 6A) (compare cells population within circle). FIG. 6C-6D compare cell viability of the cells dissociated using enzymatic dissociation (FIG. 6C) and bulk lateral ultrasonic waves (FIG. 6D), as indicated by nucleated cells (as determined by nuclear stain, x-axis) that are living (y-axis). Enzymatic dissociation resulted in approximately 7% viable cells, whereas bulk lateral ultrasonic wave dissociation resulted in about 31% viable cells.

Example 5

Dissociation of cells from a clinical breast cancer tumor extracted from a patient by bulk lateral ultrasonic energy was compared to enzymatic dissociation. Approximately 100 mg of breast cancer tissue was placed in a petri dish, to which Rosewell Park Memorial Institute (RPMI) medium was added. The breast cancer tissue sample was minced to tissue pieces about 1 $mm^3$ to about 3 $mm^3$ in size. The minced tissue sample was transferred to a sterile sample tube. The sample tube was then positioned over a transducer with 4 independently operable FASA elements having a 90° angle arranged in a circular pattern having a diameter of approximately 9 mm. Bulk lateral ultrasonic energy was applied to the sample to dissociate cells from the minced splenic tissue.

Separately, cells form a clinical breast cancer tissue sample were dissociated using an enzymatic dissociation for 45 minutes.

The samples were separately transferred to a 15 mL centrifuge tube and topped with 5 mL of wash buffer (1% bovine serum albumin (BSA) in phosphate buffered saline (PBS)). The centrifuge tubes were centrifuged at 300×g for 5 minutes at 4° C., and the supernatant was decanted. The pellet was re-suspended in 1 mL wash buffer using a wide-orifice 1 mL pipette tip before adding 5 mL ACK (Ammonium-Chloride Potassium) lysing buffer and allowing the cells to incubate at room temperature for 5-7 minutes. 5 mL of stop-reaction buffer (1% BSA in Dulbecco's Phosphate-Buffered Saline (DPBS) ($Ca^{2+}$ and $Mg^{2+}$ free)) was added to the samples, which were then centrifuged at 300×g for 5 minutes at 4° C. The supernatant was then removed, and the resulting pellet was suspended in 5 mL DPBS. The suspended cells were filtered using a 70 μm cell strainer and the filtrate topped to 5 mL using additional DPBS.

Figure 7A:
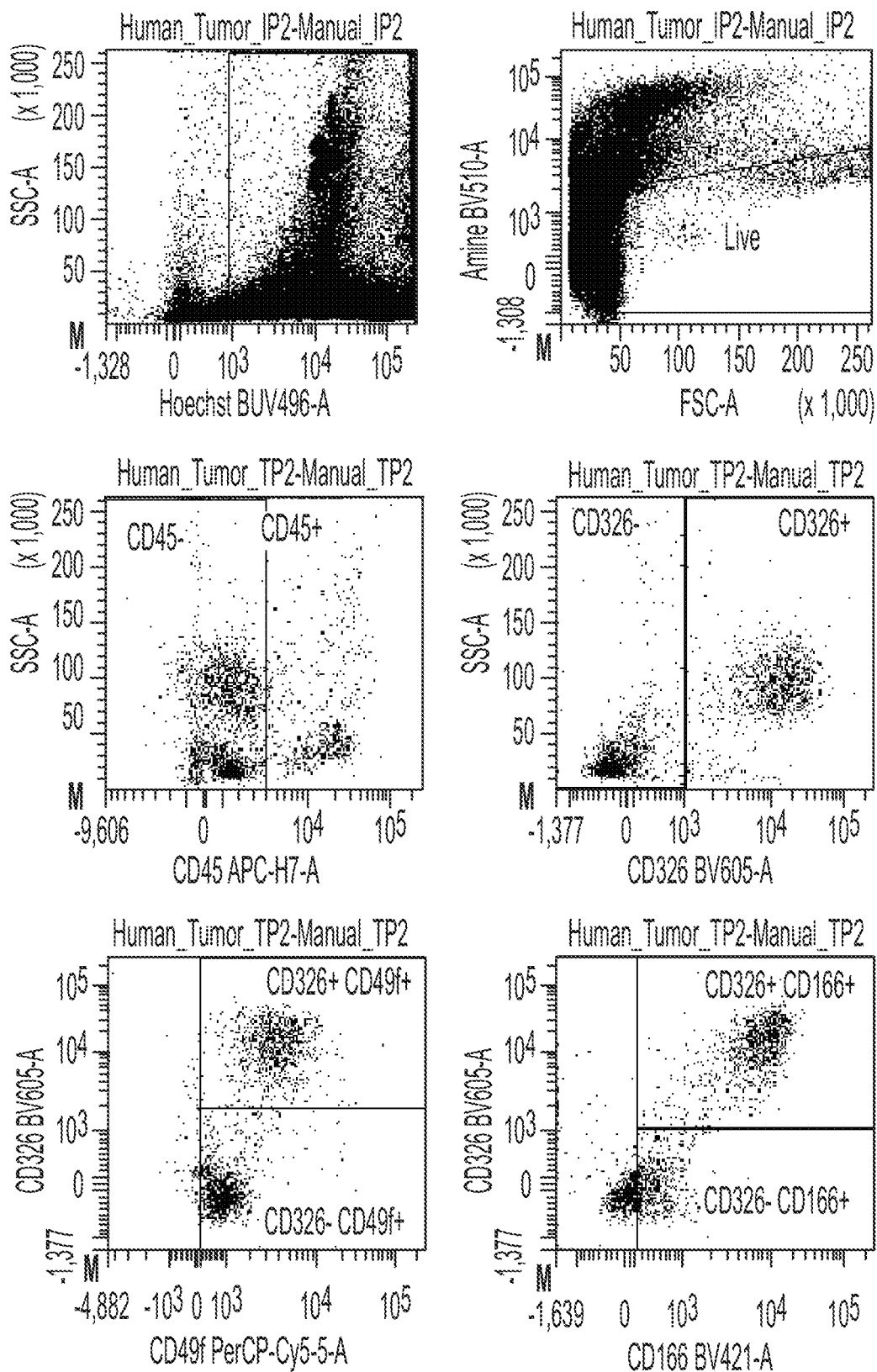
FIG. 7A shows the results of flow cytometry analysis from cells dissociated from a clinical breast cancer tumor sample using an enzymatic dissociation method.
Figure 7A:
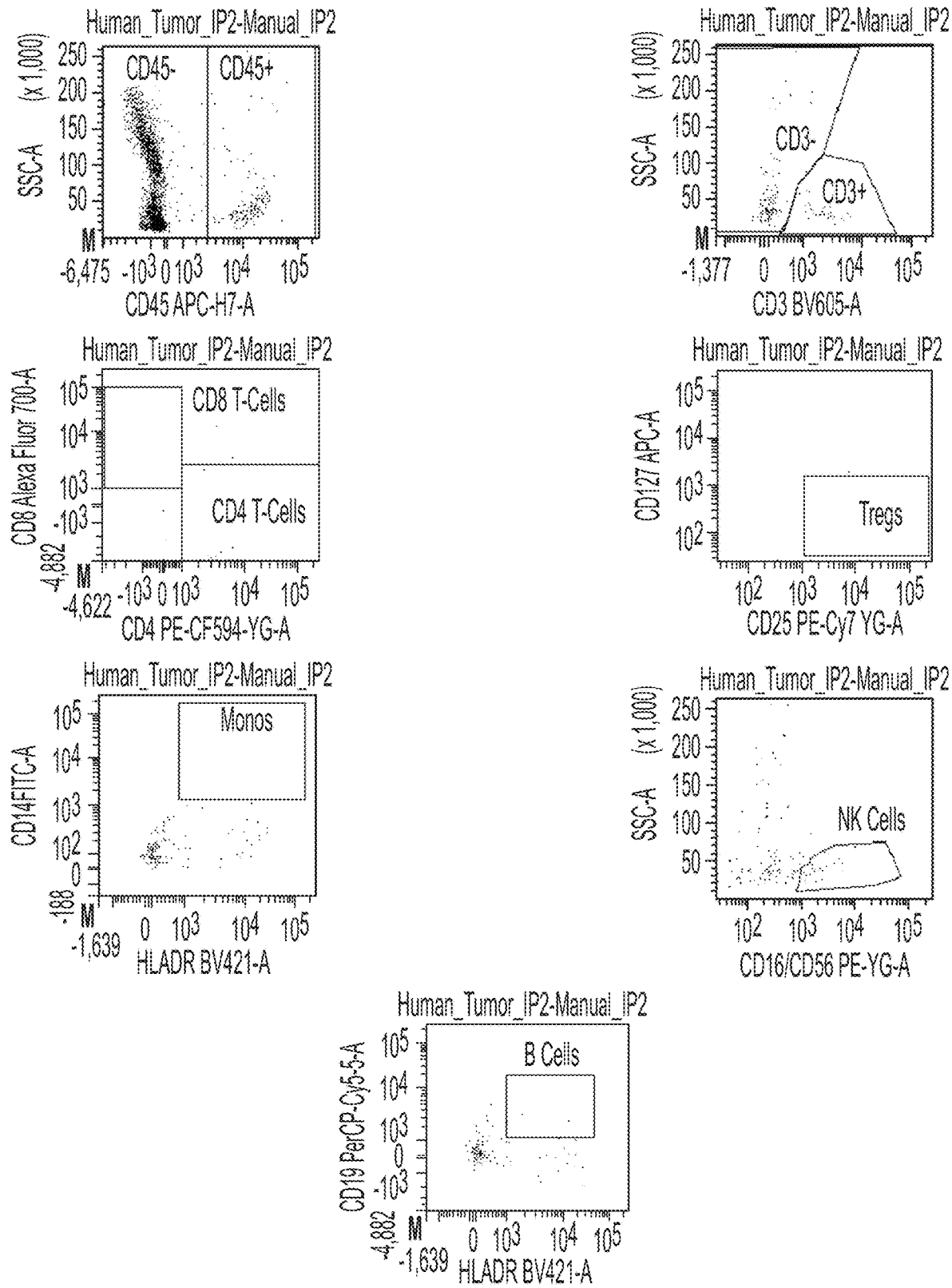
Figure 7B:
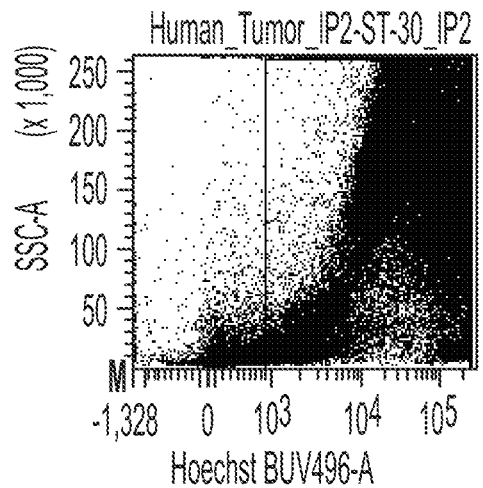
FIG. 7B shows the results of flow cytometry analysis from cells dissociated from a clinical breast cancer tumor sample using bulk lateral ultrasonic energy as described herein.
Figure 7B:
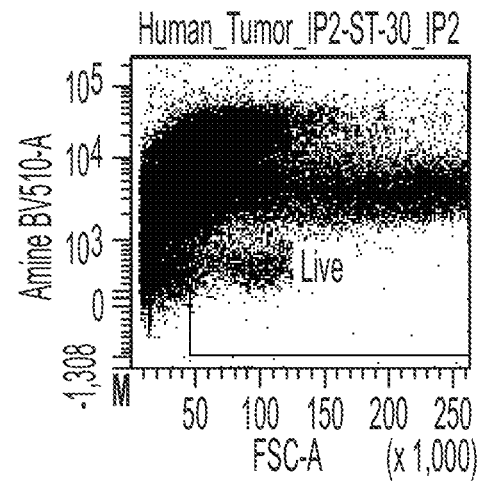
Figure 7B:
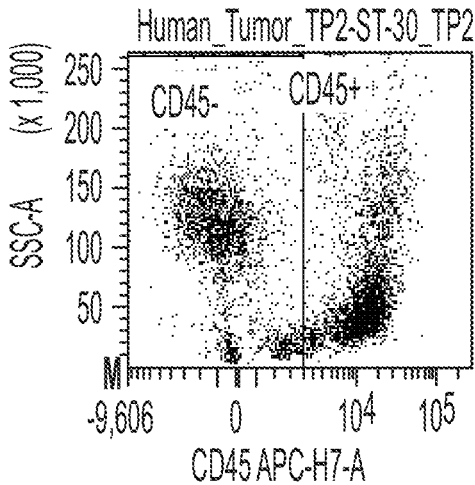
Figure 7B:
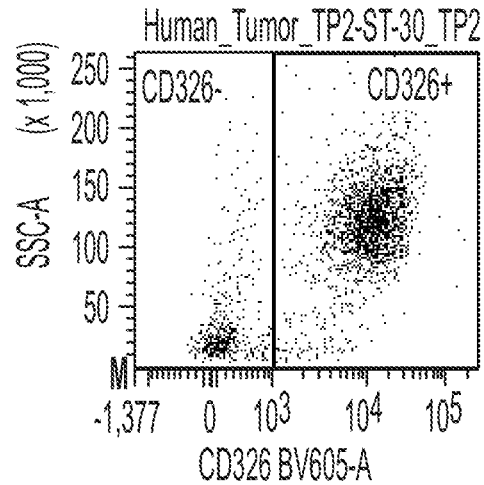
Figure 7B:
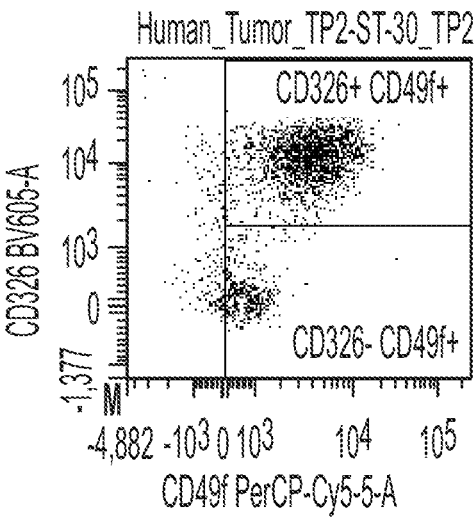
Figure 7B:
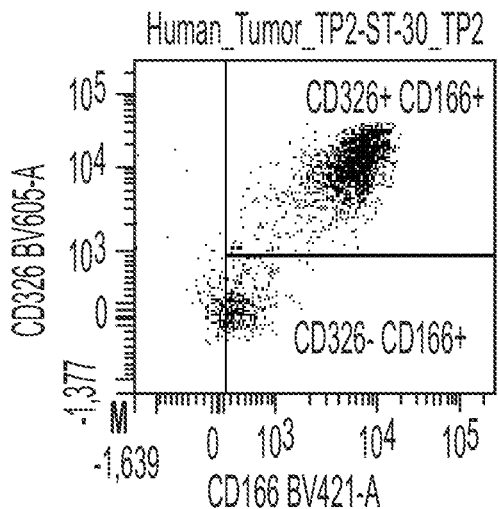
Figure 7B:
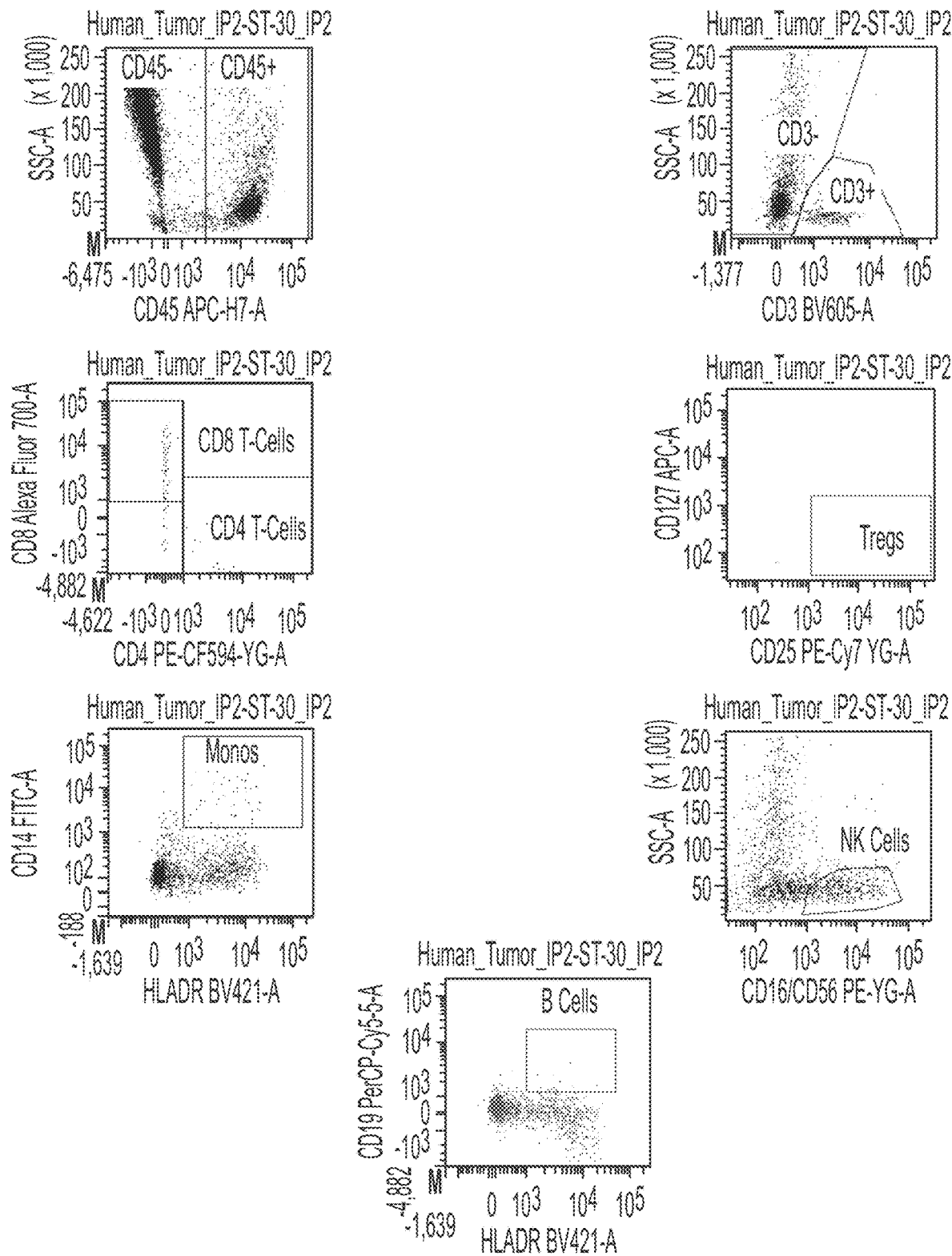

Cells from both samples were compared using flow cytometry (FACS), and results are shown in FIG. 7A (enzymatic dissociation) and FIG. 7B (bulk lateral ultrasonic energy dissociation). As shown in FIG. 7B, the bulk lateral ultrasonic energy successfully dissociated CD45– cells, CD45+ cells, CD326– cells, CD326+ cells, CD326+CD49f+ cells, CD326+CD166+ cells, CD3– cells, CD3+ cells, CD8+ T cells, CD4+ T cells, monocytes, natural killer (NK cells), and B cells from the cancer tissue.

Example 6

Dissociation of cells from a formalin-fixed paraffin-embedded (FFPE) human breast cancer xenograft (PDX) tumor biopsy obtained from a mouse model by bulk lateral ultrasonic energy was compared to enzymatic dissociation. Approximately 100 mg of the PDX tissue was placed in a petri dish, to which Rosewell Park Memorial Institute (RPMI) medium was added. The breast cancer tissue sample was minced to tissue pieces about 1 $mm^3$ to about 3 $mm^3$ in size. The minced tissue sample was transferred to a sterile sample tube. The sample tube was then positioned over a transducer with 4 independently operable FASA elements having a 90° angle arranged in a circular pattern having a diameter of approximately 9 mm. Bulk lateral ultrasonic energy was applied to the sample to dissociate cells from the minced splenic tissue.

Separately, cells form a similar FFPE human breast cancer xenograft tumor biopsy were dissociated using an enzymatic dissociation for 45 minutes.

The samples were separately transferred to a 15 mL centrifuge tube and topped with 5 mL of wash buffer (1% bovine serum albumin (BSA) in phosphate buffered saline (PBS)). The centrifuge tubes were centrifuged at 300×g for 5 minutes at 4° C., and the supernatant was decanted. The pellet was re-suspended in 1 mL wash buffer using a wide-orifice 1 mL pipette tip before adding 5 mL ACK (Ammonium-Chloride Potassium) lysing buffer and allowing the cells to incubate at room temperature for 5-7 minutes. 5 mL of stop-reaction buffer (1% BSA in Dulbecco's Phosphate-Buffered Saline (DPBS) ($Ca^{2+}$ and $Mg^{2+}$ free)) was added to the samples, which were then centrifuged at 300×g for 5 minutes at 4° C. The supernatant was then removed, and the resulting pellet was suspended in 5 mL DPBS. The suspended cells were filtered using a 70 µm cell strainer and the filtrate topped to 5 mL using additional DPBS.

Figure 8A:
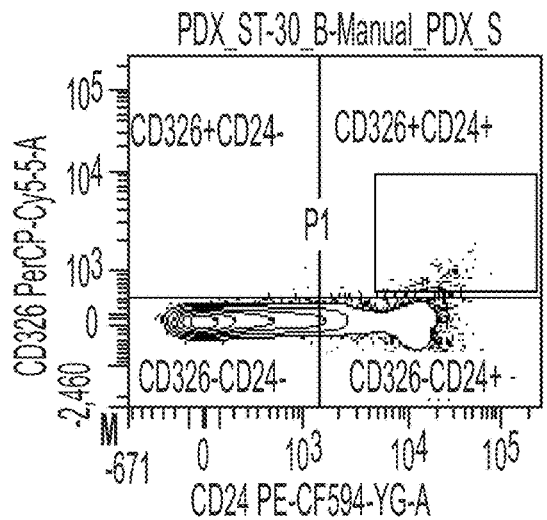
FIG. 8A shows the results of flow cytometry analysis from cells dissociated from a formalin-fixed paraffin-embedded (FFPE) human breast cancer xenograft (PDX) tumor biopsy obtained from a mouse model using an enzymatic dissociation method. The upper-right quadrant indicates the substantial absence of dissociated CD326+/CD24+ cells.
Figure 8B:
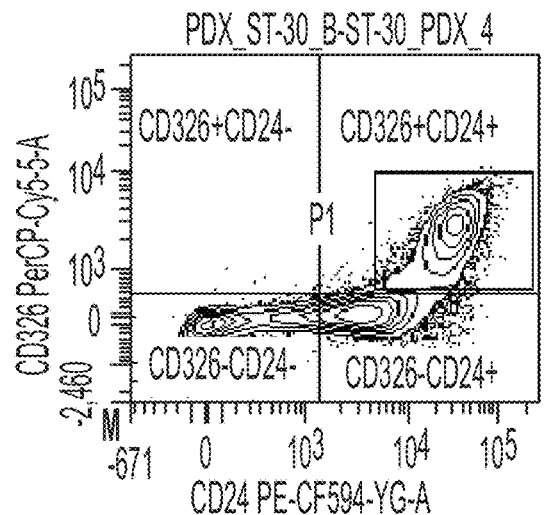
FIG. 8B shows the results of flow cytometry analysis from cells dissociated from a FFPE human breast cancer xenograft (PDX) tumor biopsy obtained from a mouse model using bulk lateral ultrasonic energy as described herein. The upper-right quadrant indicates dissociated CD326+/CD24+ cells.
Figure 8C:
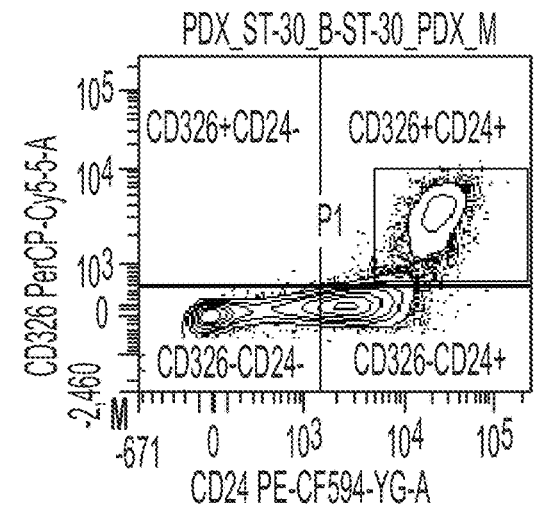
FIG. 8C shows the results of flow cytometry analysis from cells dissociated from a residual FFPE human breast cancer xenograft (PDX) tumor tissue after enzymatic dissociation, further treated using bulk lateral ultrasonic energy as described herein. The upper-right quadrant indicates dissociated CD326+/CD24+ cells which were not successfully dissociated using enzymatic methods.

Cells from both samples were compared using flow cytometry (FACS). Few CD326+, CD24+ cells dissociated from the tissue sample by enzymatic dissociation (FIG. 8A). In contrast, a significant number of CD326+, CD24+ cells dissociated from the tissue sample using bulk lateral ultrasonic energy. Further, when the residual tissue from the enzymatic dissociation sample was treated with the bulk lateral ultrasonic energy, CD326+, CD24+ cells were successfully dissociated (FIG. 8C).

Example 7

Four 45 mg tissue sample a pig liver were obtained. Two of the samples were dissociated into a cellular suspension using bulk later ultrasonic (BLU) waves. One sample was dissociated into a cellular suspension using a standard Miltenyi enzymatic tissue dissociation protocol. One sample was retained in its solid tissue state as a control sample.

The cellular suspensions and solid tissue samples were frozen before RNA was extracted and assessed for minimum RIN values for valid sequencing data. mRNA was prepared for sequencing using TruSeq™ RNA Library Pep Kit (Illumina), and then sequenced using a NextSeq™ sequencer (Illumina). The resulting data was sequenced using standard next generation sequencing data analysis tools.

Figure 9A:
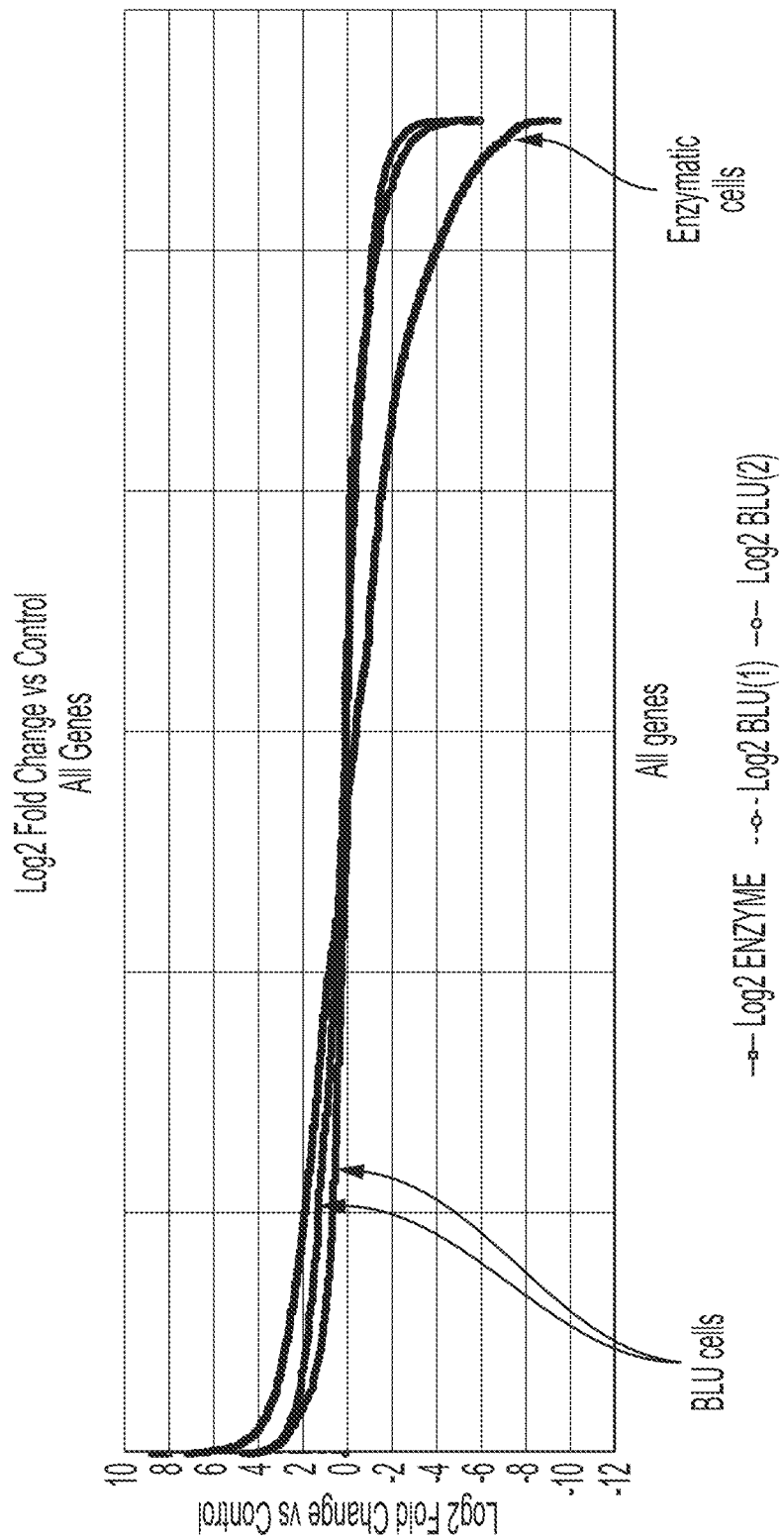
FIG. 9A shows the gene expression changes in cells dissociated from tissue by bulk lateral ultrasonic energy and cells dissociated from solid tissue using an enzymatic process, compared to a control sample (solid tissue), for all available genes.
Figure 9B:
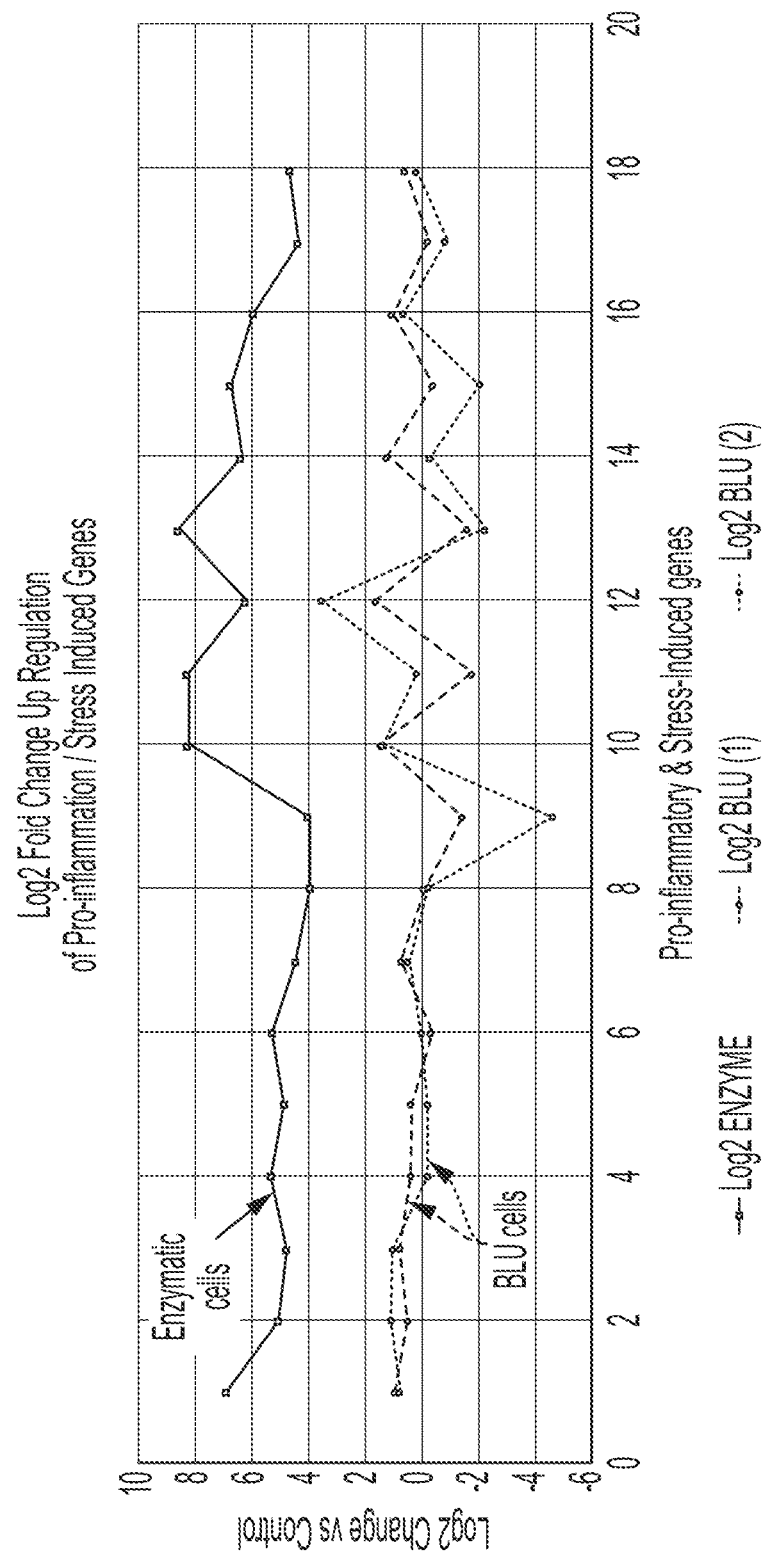
FIG. 9B shows the gene expression changes in cells dissociated from tissue by bulk lateral ultrasonic energy and cells dissociated from solid tissue using an enzymatic process, compared to a control sample (solid tissue), for pro-inflammatory or stress-induced genes.

FIG. 9A shows the fold change compared to the control sample (solid tissue) for all available genes. The gene expression profiles dissociated using bulk later ultrasonic (BLU) energy are closely aligned with the control sample tissue for most genes, while the gene expression for the cells enzymatically dissociated (ENZYME) are not as closely aligned. FIG. 9B shows the fold change compared to the control sample (solid tissue) for pro-inflammatory and stress-induced genes (CD69, LRRK2, TNF, FOS, PDE4B, NR4A3, S100A9, S100A8, THBD, IL-1β, IL-1α, HK2, CXCL8, CXCL1, AREG, EGR2, TIMP1, and CXCR4). For each of the measured pro-inflammatory and stress-induced genes, the enzymatically dissociated cells showed a higher increase in gene expression compared to the cells dissociated using bulk lateral ultrasonic waves.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

What is claimed is:

1. A method of dissociating single cells from a biological tissue sample, comprising:
generating one or more ultrasonic wave pulses using a transducer comprising one or more Fresnel Annular Sector Actuator (FASA) elements; and
applying energy from the one or more generated ultrasonic wave pulses to a biological tissue sample contained by a sample container through a coupling medium that couples the one or more FASA elements to the sample container to dissociate single cells from the biological tissue.

2. The method of claim 1, further comprising controlling the temperature of the biological tissue sample while the energy from the one or more generated ultrasonic wave pulses is applied to the biological tissue sample.

3. The method of claim 2, wherein controlling the temperature of the biological tissue sample comprises controlling the temperature of the coupling medium.

4. The method of claim 3, wherein the temperature of the coupling medium is controlled to cool the biological tissue sample or limit a temperature increase of the biological tissue sample.

5. The method of claim 3, wherein the coupling medium is controlled to a temperature between about 2° C. and about 70° C.

6. The method of claim 3, wherein the coupling medium is controlled to a temperature between about 2° C. and about 25° C.

7. The method of claim 2, wherein controlling the temperature of the biological tissue sample comprises heating the biological tissue sample using the energy from the one or more generated ultrasonic wave pulses.

8. The method of claim 7, wherein a first portion of the one or more ultrasonic wave pulses generated by the transducer are configured to heat the biological tissue sample and a second portion of the one or more ultrasonic wave pulses generated by the transducer are configured to not heat the biological tissue sample.

9. The method of claim 7, wherein the biological tissue sample is heated to a peak temperature between about 20° C. and about 70° C.

10. The method of claim 1, wherein the biological tissue sample is heated by less than 15° C. or is not heated during the application of energy from the one or more generated ultrasonic wave pulses to the sample container.

11. The method of claim 2, wherein the temperature of the biological tissue sample is controlled to between about 2° C. and about 70° C.

12. The method of claim 2, wherein controlling the temperature of the biological tissue sample reduces the expression of one or more pro-inflammatory or stressed-induced genes compared to not controlling the temperature of the biological tissue sample.

13. The method of claim 12, wherein the one or more pro-inflammatory or stressed-induced genes is selected from the group consisting of CD69, LRRK2, TNF, FOS, PDE4B, NR4A3, S100A9, S100A8, THBD, IL-1β, IL-1α, HK2, CXCL8, CXCL1, AREG, ERG2, TIMP1, and CXCR4.

14. The method of claim 1, wherein the coupling medium is a liquid, a solid, or a gel.

15. The method of claim 1, wherein the coupling medium is a liquid, the method further comprising cycling the coupling fluid through a temperature controller.

16. The method of claim 1, wherein about 20% or more of the dissociated single cells are viable.

17. The method of claim 16, wherein about 20% to about 95% of the dissociated single cells are viable.

18. The method of claim 1, wherein two or more different types of viable cells are dissociated from the biological tissue sample.

19. The method of claim 1, wherein the biological tissue sample comprises a cancer tissue.

20. The method of claim 1, wherein the energy applied to the sample does not result in a shear force applied to the sample.

21. The method of claim 1, comprising selecting one or more of a repetition rate, a pulse duration, a duty cycle, a peak power, or a total duration for the one or more generated ultrasonic wave pulses.

22. The method of claim 1, wherein the energy applied to the sample results in a mixing force or a suspending force applied to the sample.

23. The method of claim 1, wherein the biological tissue is suspended in a liquid within the sample container.

24. The method of claim 1, wherein the biological tissue is minced.

25. The method of claim 1, wherein the biological tissue sample is substantially free of non-endogenous proteases.

26. The method of claim 1, wherein the transducer comprises four or more FASA elements.

27. The method of claim 1, wherein the biological tissue sample is an unpreserved sample.

28. A system for dissociating single cells from a biological tissue sample, comprising:
- a transducer comprising one or more Fresnel Annular Sector Actuator (FASA) elements configured to generate one or more ultrasonic wave pulses;
- a sample container configured to hold the biological tissue sample; and
- a coupling medium configured to couple the one or more FASA elements to the sample container and transmit energy from the plurality of ultrasonic wave pulses generated by the transducer to the sample container to dissociate single cells from the biological tissue sample.

29. The system of claim 28, further comprising a temperature controller configured to control the temperature of the biological tissue sample.

* * * * *